United States Patent
Wardleworth et al.

(10) Patent No.: US 7,256,188 B2
(45) Date of Patent: Aug. 14, 2007

(54) 3-AMINOALKYL-2-ARYL-INDOLE DERIVATIVES AND THEIR USE AS GNRH ANTAGONISTS

(75) Inventors: Michael Wardleworth, Chesire (GB); Alexander Graham Dossetter, Chesire (GB); Christopher Thomas Halsall, Lancashire (GB)

(73) Assignee: AstraZeneca AB, Södertälje (SE)

(*) Notice: Subject to any disclaimer, the term of this patent is extended or adjusted under 35 U.S.C. 154(b) by 362 days.

(21) Appl. No.: 10/477,795

(22) PCT Filed: May 8, 2002

(86) PCT No.: PCT/GB02/02116

§ 371 (c)(1),
(2), (4) Date: Mar. 1, 2004

(87) PCT Pub. No.: WO02/092565

PCT Pub. Date: Nov. 21, 2002

(65) Prior Publication Data
US 2004/0142987 A1    Jul. 22, 2004

(30) Foreign Application Priority Data
May 14, 2001    (SE)    ................................ 0101692

(51) Int. Cl.
*A61K 31/5377*    (2006.01)
*A61K 31/495*    (2006.01)
*C07D 209/04*    (2006.01)
*C07D 403/12*    (2006.01)
*C07D 413/12*    (2006.01)

(52) U.S. Cl. .................. 514/235.2; 544/106; 544/111; 544/141; 544/143; 544/224; 544/336; 544/359; 544/373; 546/268.1; 546/276.4; 546/277.4; 548/452; 548/465; 514/231.2; 514/233.5; 514/254.01; 514/339

(58) Field of Classification Search ................ 544/106, 544/111, 141, 143, 224, 336, 358, 373; 546/268.1, 546/277.4; 548/452, 465; 514/231.2, 235.2, 514/254.01, 331, 339
See application file for complete search history.

(56) References Cited

U.S. PATENT DOCUMENTS 5,580,957 A * 12/1996 Hoeger et al. .............. 530/345
5,756,507 A * 5/1998 Goulet et al. .......... 514/254.08
6,809,098 B2 * 10/2004 Wardleworth et al. ... 514/235.2

FOREIGN PATENT DOCUMENTS

| WO | 97/21704 A1 | 6/1997 |
|---|---|---|
| WO | 97/21707 A1 | 6/1997 |
| WO | WO-97/21435 A | 6/1997 |
| WO | WO-97/21703 A | 6/1997 |
| WO | 98/55116 A1 | 12/1998 |
| WO | 98/55119 A1 | 12/1998 |
| WO | 98/55123 A1 | 12/1998 |
| WO | 98/55470 A1 | 12/1998 |
| WO | 98/55479 A1 | 12/1998 |
| WO | 99/21557 A1 | 5/1999 |
| WO | WO-99/21553 A | 5/1999 |
| WO | 99/41251 A1 | 8/1999 |
| WO | 99/41252 A1 | 8/1999 |
| WO | 99/51231 A1 | 10/1999 |
| WO | 99/51232 A1 | 10/1999 |
| WO | 99/51233 A1 | 10/1999 |
| WO | 99/51234 A1 | 10/1999 |
| WO | 99/51595 A1 | 10/1999 |
| WO | 99/51596 A1 | 10/1999 |
| WO | 00/04013 A1 | 1/2000 |
| WO | 00/53178 A1 | 9/2000 |
| WO | 00/53179 A1 | 9/2000 |
| WO | 00/53180 A1 | 9/2000 |
| WO | 00/53181 A1 | 9/2000 |
| WO | 00/53185 A1 | 9/2000 |

(Continued)

OTHER PUBLICATIONS

Chu, L., et al., "Initial structure-activity relationship of a novel class of nonpeptidyl GnRH receptor antagonists: 2-arylindoles," Bioorganic & Medicinal Chemistry Letters, Oxford, GB, vol. 11, No. 4, 509-513 (Feb. 26, 2001) XP004230047.

Chu, L., et al., "SAR studies of novel 5-substituted 2-arylindoles as nonpeptidyl GnRH receptor antagonists," Bioorganic & Medicinal Chemistry Letters, Oxford, GB, vol. 11, No. 4, 515-517 (Feb. 26, 2001) XP004230048.

(Continued)

*Primary Examiner*—Golam M. M. Shameem

(57) ABSTRACT

The present invention relates to compounds of formula I which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds 10 Claims, No Drawings

FOREIGN PATENT DOCUMENTS

| WO | 00/53602 A1 | 9/2000 |
|---|---|---|
| WO | 00/69433 A1 | 11/2000 |
| WO | WO-02/066459 A | 8/2002 |

OTHER PUBLICATIONS

Lin, P., et al., "Heterocyclic Derivatives of 2-(3,5-Dimethylphenyl)tryptamine as GnRH Receptor Antagonists," Bioorganic & Medicinal Chemistry Letters, Oxford, GB, vol. 11, No. 8, 1077-1080 (Apr. 23, 2001) XP002217298.

Simeone, J.P., et al., "Modification of the Pyridine Moiety of Non-peptidyl Indole GnHR Receptor Antagonists," Bioorganic & Medicinal Chemistry Letters, 12, 3329-3332 (2002).

Ujjainwalla F., et al., "Total synthesis of 6- and 7-azaindole derived GnHR antagonists," Tetrahedron Letters 42, 6441-6445 (2001).

Gibbs, J.B., et al., "Pharmaceutical Research in Molecular Oncology," Cell, 79(2), 193-198 (1994).

Ashton, W.T., Substituted Indole-5-carboxamides and -acetamides as Potent Nonpeptide GnRH Receptor Antagonist, Bioorganic & Medicinal Chemistry Letters, 2001, 1723-1726, vol. 11.

Ashton et. al., Potent Nonpeptide GnHR Receptor Antagonists Derived from Substituted Indole-5-carboxamides and -acetamides Bearing a Pyridine Side-Chain Terminus, Bioorganic & Medicinal Chemistry Letters, 2001, 1727-1731, vol. 11.

Ashton et. al., Orally Bioavailable, Indole-Based Nonpeptide GnHR Receptor Antagonists with High Potency and Functional Activity, Bioorganic and Medicinal Chemistry Letters, 2001, 2597-2602, vol. 11.

Freidinger, R. M., Nonpeptidic ligands for peptide and protein receptors, Current Opinion in Chemical Biology, 1999, 395-406, vol. 3.

Goulet, M. T., Gonadotropin Releasing Hormone Antagonists, Annual Reports in Medicinal Chemistry, 1995, 169-178, vol. 30.

Lin, P. et al., 2-(3,5-Dimethylphenyl)tryptamine Derivatives That Bind to the GnHR Receptor, Bioorganic & Medicinal Chemistry Letters, 2001, 1073-1076, vol. 11.

Simoene et. al., Synthesis of chiral B-methyl tryptamine-derived GnHR antagonists, Tetrahedron Letters, 2001, 6459-6461, vol. 42.

Walsh et. al., A convergent synthesis of (S)-B-methyl-2-aryltryptamine based gonadotropin releasing hormone antagonists, Tetrahedron, 2001, 5233-5241, vol. 57.

Young et. al., 2-Arylindoles as Gonadotropin Releasing Hormone (GnHR) Antagonists: Optimization of the Tryptamine Side Chain, Bioorganic & Medicinal Chemistry Letters, 2002, 827-832, vol. 12.

* cited by examiner

3-AMINOALKYL-2-ARYL-INDOLE DERIVATIVES AND THEIR USE AS GNRH ANTAGONISTS

CROSS-REFERENCE TO RELATED APPLICATIONS

This application is a national stage filing under 35 U.S.C. 371 of International Application No. PCT/GB02/02116, filed May 8, 2002, which claims priority from Sweden Application No. 0101692-2, filed May 14, 2001, the specification of which is incorporated by reference herein. International Application No. PCT/GB02/02116 was published under PCT Article 21(2) in English.

FIELD OF THE INVENTION

The present invention relates to compounds which are antagonists of gonadotropin releasing hormone (GnRH) activity. The invention also relates to pharmaceutical formulations, the use of a compound of the present invention in the manufacture of a medicament, a method of therapeutic treatment using such a compound and processes for producing the compounds.

BACKGROUND OF INVENTION

Gonadotropin releasing hormone (GnRH) is a decapeptide that is secreted by the hypothalamus into the hypophyseal portal circulation in response to neural and/or chemical stimuli, causing the biosynthesis and release of luteinizing hormone (LH) and follicle-stimulating hormone (FSH) by the pituitary. GnRH is also known by other names, including gonadoliberin, LH releasing hormone (LHRH), FSH releasing hormone (FSH RH) and LH/FSH releasing factor (LH/FSH RF).

GnRH plays an important role in regulating the action of LH and FSH (by regulation of their levels), and thus has a role in regulating the levels of gonadal steroids in both sexes, including the sex hormones progesterone, oestrogens and androgens. More discussion of GnRH can be found in WO 98/5519 and WO 97/14697, the disclosures of which are incorporated herein by reference.

It is believed that several diseases would benefit from the regulation of GnRH activity, in particular by antagonising such activity. These include sex hormone related conditions such as sex hormone dependent cancer, benign prostatic hypertrophy and myoma of the uterus. Examples of sex hormone dependent cancers are prostatic cancer, uterine cancer, breast cancer and pituitary gonadotrophe adenoma.

The following disclose compounds purported to act as GnRH antagonists: WO 97/21435, WO 97/21703, WO 97/21704, WO 97/21707, WO 55116, WO 98/55119, WO 98/55123, WO 98/55470, WO 98/55479, WO 99/21553, WO 99/21557, WO 99/41251, WO 99/41252, WO 00/04013, WO 00/69433, WO 99/51231, WO 99/51232, WO 99/51233, WO 99/51234, WO 99/51595, WO 99/51596, WO 00/53178, WO 00/53180, WO 00/53179, WO 00/53181, WO 00/53185 and WO 00/53602.

It would be desirable to provide further compounds, such compounds being GnRH antagonists.

SUMMARY OF THE INVENTION

The present invention accordingly provides a compound of formula I or a salt, pro-drug or solvate thereof

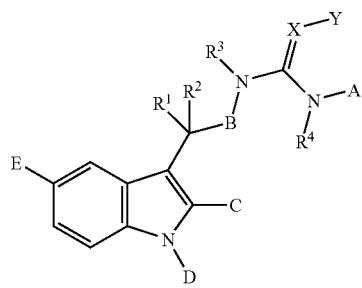

Formula I wherein for A, either:—
(i) A represents hydrogen or optionally-substituted $C_1$ to $C_8$ alkyl; or
(ii) the structure N—A(—$R^4$) represents an optionally-substituted 3- to 8-membered heterocyclic ring optionally containing from 1 to 3 further heteroatoms independently selected from O, N and S;

B represents a direct bond or optionally substituted $C_1$ to $C_5$ alkylene;

C represents a mono- or bi-cyclic aromatic ring structure optionally having at least one substituent selected from CN, $NR^5R^6$, an optionally substituted $C_1$ to $C_8$ alkyl, optionally substituted $C_1$ to $C_8$ alkoxy or halo;

D represents hydrogen; optionally substituted $C_1$ to $C_8$ alkyl; or $(CH_2)_b$—$R^a$, wherein $R^a$ represents $C_3$ to $C_8$ cycloalkyl and b is zero or an integer from 1 to 6;

E is selected from an optionally substituted 3- to 8-membered heterocyclic ring containing from 1 to 4 heteroatoms independently selected from O, N and S; or a group of formula II; III; IV; V; VI; VII or VIII

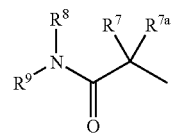

II

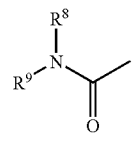

III

IV

V

VI

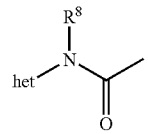

VII

-continued

VIII wherein het represents an optionally substituted 3- to 8-membered heterocyclic ring containing from 1 to 4 heteroatoms independently selected from O, N and S;

for X and Y, either:—
(iii) X represents N and Y represents CN; hydrogen or —CONR$^b$R$^c$ where R$^b$ and R$^c$ are independently selected from hydrogen and C$_1$ to C$_8$ alkyl;
(iiia) X represents CH and Y represents NO$_2$; or
(iv) X—Y represents O;

for R$^1$ and R$^2$, either:—
(v) R$^1$ and R$^2$ are independently selected from hydrogen and optionally substituted C$_1$ to C$_8$ alkyl; or
(vi) R$^1$ and R$^2$ together represent carbonyl; or
(vii)

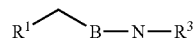

represents an optionally substituted 3- to 8-membered heterocyclic ring containing from 1 to 3 further heteroatoms independently selected from O, N and S, and R$^2$ meets the definition in option (v);
R$^3$ meets the definition in option (vii) or represents hydrogen or optionally substituted C$_1$ to C$_8$ alkyl;
R$^4$ meets the definition in option (ii) or when A meets the definition in option (i) R$^4$ represents hydrogen or optionally substituted C$_1$ to C$_8$ alkyl;
R$^5$ and R$^6$ are independently selected from hydrogen; optionally substituted C$_1$ to C$_8$ alkyl and optionally substituted aryl;

for R$^7$ and R$^{7a}$, either:—
(viii) R$^7$ and R$^{7a}$ are independently selected from hydrogen or optionally substituted C$_1$ to C$_8$ alkyl; or
(ix)

represents an optionally substituted 3 to 7-membered cycloalkyl ring;

For R$^8$ and R$^9$, either:—
(x) R$^8$ is selected from hydrogen; optionally substituted C$_1$ to C$_8$ alkyl; optionally substituted aryl; —R$^d$—Ar, where R$^d$ represents C$_1$ to C$_8$ alkylene and Ar represents optionally substituted aryl; and optionally substituted 3- to 8-membered heterocyclic ring optionally containing from 1 to 3 further heteroatoms independently selected from O, N and S; and
R$^9$ is selected from hydrogen; optionally substituted C$_1$ to C$_8$ alkyl and optionally substituted aryl;
(xi) wherein E represents a group of formula II or III, then the group NR$^8$(—R$^9$) represents an optionally substituted 3- to 8-membered heterocyclic ring optionally containing from 1 to 3 further heteroatoms independently selected from O, N and S; or (xii) wherein E represents structure VI, represents an optionally substituted 3- to 8-membered heterocyclic ring optionally containing from 1 to 4 heteroatoms independently selected from O, N and S;

with the proviso that:

when A is C$_1$ to C$_8$ alkyl or the structure N—A(—R$^4$) represents an optionally-substituted 3- to 8-membered heterocyclic ring containing from 1 to 3 heteroatoms independently selected from O, N and S; X represents N and Y represents CN or hydrogen, X represents CH and Y represents NO$_2$ or X—Y represents O; then the optional substituents on A are not selected from optionally substituted phenyl or an optionally-substituted 3- to 8-membered heterocyclic ring.

The present invention also provides a pharmaceutical formulation comprising such a compound, or salt, pro-drug or solvate thereof, and a pharmaceutically acceptable diluent or carrier.

Furthermore, the present invention provides the following uses of the compound, or salt, pro-drug or solvate thereof:—
(a) use in the manufacture of a medicament for antagonising gonadotropin releasing hormone activity;
(b) use in the manufacture of a medicament for administration to a patient, for reducing the secretion of luteinizing hormone by the pituitary gland of the patient; and
(c) use in the manufacture of a medicament for administration to a patient, for therapeutically treating and/or preventing a sex hormone related condition in the patient.

The present invention also relates to a method of antagonising gonadotropin releasing hormone activity in a patient, comprising administering the compound, or salt, pro-drug or solvate thereof, to the patient.

In addition, the invention provides a process of producing the compound, or salt, pro-drug or solvate thereof.

DETAILED DESCRIPTION OF THE INVENTION

As discussed above, the present invention provides a compound of formula I or a salt, pro-drug or solvate thereof

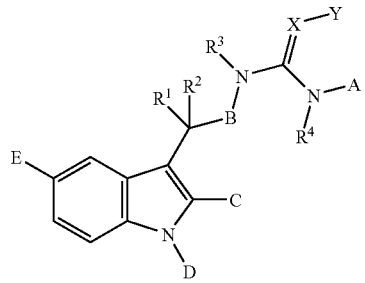

Formula I wherein for A, either:—
(i) A represents hydrogen or optionally-substituted C$_1$ to C$_8$ alkyl (preferably, C$_1$ to C$_4$ alkyl, for example methyl or ethyl); or (ii) the structure N—A(—R$^4$) represents a optionally-substituted 3- to 8-membered heterocyclic ring (preferably, a 5- or 6-membered monocyclic ring) optionally containing from 1 to 3 (eg, 1) further heteroatoms independently selected from O, N and S.

When the structure N—A(—R$^4$) represents a 3- to 8-membered heterocyclic ring, the heterocyclic ring is preferably selected from an optionally-substituted group of formula, IX, X and XI:

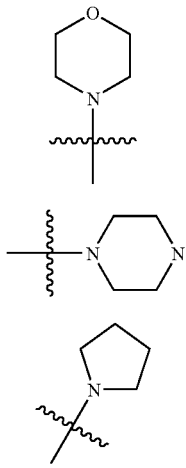

IX

X

XI

Further preferably when the structure N—A(—R$^4$) represents a 3- to 8-membered heterocyclic ring, the heterocyclic ring is selected from a group of formula XII or XIII:

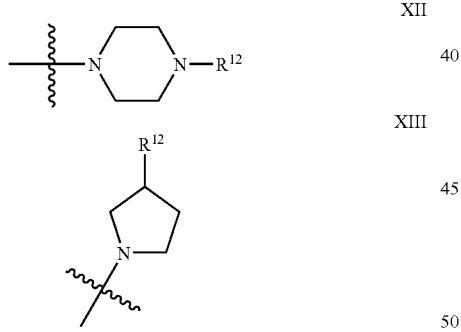

XII

XIII wherein R$^{12}$ represents $C_1$ to $C_8$ alkyl; —(CH$_2$)$_c$NR$^e$R$^f$, where c is zero or an integer from 1 to 4, and R$^e$ and R$^f$ independently represent hydrogen or $C_1$ to $C_8$ alkyl; hydroxy; halo; CN; $C_1$ to $C_8$ alkoxy; or CF$_3$.

B represents a direct bond or optionally substituted $C_1$ to $C_5$ alkylene (preferably, $C_1$ to $C_4$ alkylene, for example methylene or ethylene).

C represents a mono- or bi-cyclic aromatic ring structure (preferably, phenyl) optionally having at least one substituent (eg, 1, 2 or 3 substituents) selected from CN, NR$^5$R$^6$, an optionally substituted $C_1$ to $C_8$ alkyl (preferably, $C_1$ to $C_4$ alkyl, eg, methyl or ethyl), optionally substituted $C_1$ to $C_8$ alkoxy (preferably, $C_1$ to $C_6$ alkoxy, eg, methoxy, ethoxy or tert-butoxy) or halo (eg, F, Br or Cl).

Preferably, C represents

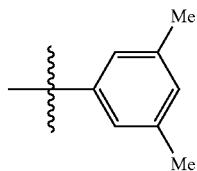

wherein Me represents methyl.

D represents hydrogen; optionally substituted $C_1$ to $C_8$ alkyl (preferably, $C_1$ to $C_6$ alkyl, eg, methyl, ethyl or tert-butyl); or (CH$_2$)$_b$—R$^a$, wherein R$^a$ represents $C_3$ to $C_8$ cycloalkyl (eg, $C_3$, $C_4$, $C_5$ or $C_6$ cycloalkyl) and b is zero or an integer from 1 to 6.

E is selected from an optionally substituted 3- to 8-membered heterocyclic ring (preferably, a 5- or 6-membered monocyclic ring) containing from 1 to 4 (eg, 1 or 2) heteroatoms independently selected from O, N and S; or a group of formula II; III; IV; V; VI; VII or VIII

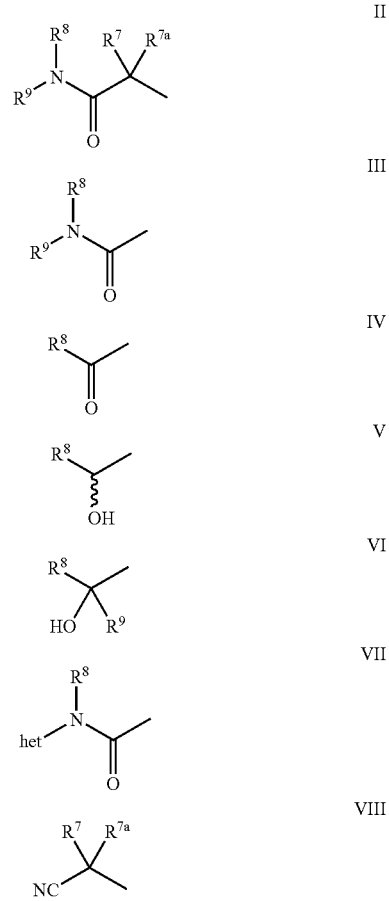

II

III

IV

V

VI

VII

VIII wherein het represents an optionally substituted 3- to 8-membered heterocyclic ring (preferably, a 5- or 6-membered monocyclic ring) containing from 1 to 4 (eg, 1 or 2) heteroatoms independently selected from O, N and S.

Preferably, E represents
(a) structure II of the sub-formula

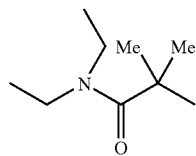

wherein Me represents methyl;
(b) structure II, wherein

represents cyclopropyl or cyclobutyl; or
(c) structure VIII wherein $R^7$ and $R^{7a}$ each represent methyl.

For X and Y, either:—
(iii) X represents N and Y represents CN; hydrogen or —$CONR^bR^c$ where $R^b$ and $R^c$ are independently selected from hydrogen and $C_1$ to $C_8$ alkyl;
(iiia) X represents CH and Y represents $NO_2$; or
(iv) X—Y represents O.

Preferably X and Y represent either:—
(a) X represents CH and Y represents $NO_2$;
(b) X represents N and Y represents CN; or
(c) X represents N and Y represents hydrogen.

Further preferably X and Y represent either:—
(a) X represents CH and Y represents $NO_2$; or
(b) X represents N and Y represents CN;

In a further embodiment of the invention X represents N and Y represents —$CONR^bR^c$ wherein $R^b$ and $R^c$ are as defined above.

For $R^1$ and $R^2$ either:—
(v) $R^1$ and $R^2$ are independently selected from hydrogen and optionally substituted $C_1$ to $C_8$ alkyl (preferably, $C_1$ to $C_6$ alkyl, eg, methyl, ethyl or tert-butyl); or
(vi) $R^1$ and $R^2$ together represent carbonyl; or
(vii)

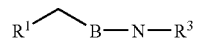

represents an optionally substituted 3- to 8-membered heterocyclic ring (preferably, a 5- or 6-membered monocyclic ring) containing from 1 to 3 (eg, 1 or 2) further heteroatoms independently selected from O, N and S, and $R^2$ meets the definition in option (v).

In one embodiment, $R^1$ and $R^2$ each represent hydrogen and B represents $C_1$ alkylene.
In a further embodiment of the invention $R^1$ represents H, $R^2$ represents methyl and B represents $C_1$ alkylene.
$R^3$ meets the definition in option (vii) or represents hydrogen or optionally substituted $C_1$ to $C_8$ alkyl (preferably, $C_1$ to $C_6$ alkyl, eg, methyl, ethyl or tert-butyl).
$R^4$ meets the definition in option (ii) or when A meets the definition in option (i) $R^4$ represents hydrogen or optionally substituted $C_1$ to $C_8$ alkyl (preferably, $C_1$ to $C_6$ alkyl, eg, methyl, ethyl or tert-butyl).
$R^5$ and $R^6$ are independently selected from hydrogen; optionally substituted $C_1$ to $C_8$ alkyl (preferably, $C_1$ to $C_6$ alkyl, eg, methyl, ethyl or tert-butyl); and optionally substituted aryl (eg, phenyl).

For $R^7$ and $R^{7a}$, either:—
(viii) $R^7$ and $R^{7a}$ are independently selected from hydrogen or optionally substituted $C_1$ to $C_8$ alkyl (preferably, $C_1$ to $C_6$ alkyl, eg, methyl, ethyl or tert-butyl; in one embodiment $R^7$ and $R^{7a}$ are both methyl); or
(ix)

represents an optionally substituted 3 to 7-membered (eg, 3-, 4-, 5- or 6-membered) cycloalkyl ring;

For $R^8$ and $R^9$, either:—
(x) $R^8$ is selected from hydrogen; optionally substituted $C_1$ to $C_8$ alkyl (preferably, $C_1$ to $C_6$ alkyl, eg, methyl, ethyl or tert-butyl; in one embodiment both $R^8$ and $R^9$ are ethyl); optionally substituted aryl (eg, optionally substituted phenyl); —$R^d$—Ar, where $R^d$ represents $C_1$ to $C_8$ alkylene (preferably, $C_1$ to $C_6$ alkylene, eg, methylene or ethylene) and Ar represents optionally substituted aryl (eg, optionally substituted phenyl); and an optionally substituted 3- to 8-membered heterocyclic ring (preferably, a 5- or 6-membered monocyclic ring) containing from 1 to 3 (eg, 1 or 2) further heteroatoms independently selected from O, N and S; and
$R^9$ is selected from hydrogen; optionally substituted $C_1$ to $C_8$ alkyl (preferably, $C_1$ to $C_6$ alkyl, eg, methyl, ethyl or tert-butyl) and optionally substituted aryl (eg, optionally substituted phenyl); or
(xi) wherein E represents a group of formula II or III, then the group $NR^8(-R^9)$ represents an optionally substituted 3- to 8-membered heterocyclic ring (preferably, a 5- or 6-membered monocyclic ring) containing from 1 to 3 (eg, 1 or 2) further heteroatoms independently selected from O, N and S; or
(xii) wherein E represents structure VI,

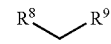

represents an optionally substituted 3- to 8-membered heterocyclic ring (preferably, a 5- or 6-membered monocyclic ring) containing from 1 to 4 (eg, 1 or 2) heteroatoms independently selected from O, N and S;

with the proviso that:

when A is $C_1$ to $C_8$ alkyl or the structure N—A(—$R^4$) represents an optionally-substituted 3- to 8-membered heterocyclic ring containing from 1 to 3 heteroatoms independently selected from O, N and S; X represents N and Y represents CN or hydrogen, X represents CH and Y represents $NO_2$ or X—Y represents O; then the optional substituents on A are not selected from optionally substituted phenyl or an optionally-substituted 3- to 8-membered heterocyclic ring.

Whilst pharmaceutically-acceptable salts of compounds of the invention are preferred, other non-pharmaceuticallyacceptable salts of compounds of the invention may also be useful, for example in the preparation of pharmaceutically-acceptable salts of compounds of the invention.

In the present specification, unless otherwise indicated, an alkyl, alkylene or alkenyl moiety may be linear or branched.

The term "alkylene" refers to the group —CH$_2$—. Thus, C$_8$ alkylene for example is —(CH$_2$)$_8$—.

The term "aryl" refers to phenyl or naphthyl.

The term "carbamoyl" refers to the group —CONH$_2$.

The term "halo" refers to fluoro, chloro, bromo or iodo.

The term "heterocyclic ring" refers to a 5-10 membered aromatic mono or bicyclic ring or a 5-10 membered saturated or partially saturated mono or bicyclic ring, said aromatic, saturated or partially unsaturated rings containing up to 5 heteroatoms independently selected from nitrogen, oxygen or sulphur, linked via ring carbon atoms or ring nitrogen atoms where a bond from a nitrogen is allowed, for example no bond is possible to the nitrogen of a pyridine ring, but a bond is possible through the 1-nitrogen of a pyrazole ring. Examples of 5- or 6-membered aromatic heterocyclic rings include pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. A 9 or 10 membered bicyclic aromatic heterocyclic ring is an aromatic bicyclic ring system comprising a 6-membered ring fused to either a 5 membered ring or another 6 membered ring. Examples of 5/6 and 6/6 bicyclic ring systems include benzofuranyl, benzimidazolyl, benzthiophenyl, benzthiazolyl, benzisothiazolyl, benzoxazolyl, benzisoxazolyl, indolyl, pyridoimidazolyl, pyrimidoimidazolyl, quinolinyl, isoquinolinyl, quinoxalinyl, quinazolinyl, phthalazinyl, cinnolinyl and naphthyridinyl. Examples of saturated or partially saturated heterocyclic rings include pyrrolinyl, pyrrolidinyl, morpholinyl, piperidinyl, piperazinyl, dihydropyridinyl and dihydropyrimidinyl.

The term "aromatic ring" refers to a 5-10 membered aromatic mono or bicyclic ring optionally containing up to 5 heteroatoms independently selected from nitrogen, oxygen or sulphur. Examples of such "aromatic rings" include: phenyl, pyrrolyl, furanyl, imidazolyl, triazolyl, pyrazinyl, pyrimidinyl, pyridazinyl, pyridinyl, isoxazolyl, oxazolyl, 1,2,4 oxadiazolyl, isothiazolyl, thiazolyl and thienyl. Preferred aromatic rings include 'phenyl, thienyl and pyridyl.

The symbol

denotes where the respective group is linked to the remainder of the molecule.

Where optional substitution is mentioned at various places, this refers to one, two, three or more optional substituents. Unless otherwise indicated above (ie, where a list of optional substituents is provided), each substituent can be independently selected from C$_1$ to C$_8$ alkyl (eg, C$_2$ to C$_6$ alkyl, and most preferably methyl, ethyl or tert-butyl); C$_3$ to C$_8$ cycloalkoxy, preferably cyclopropoxy, cyclobutoxy or cyclopentoxy; C$_1$ to C$_6$ alkoxy, preferably methoxy or C$_2$ to C$_4$ alkoxy; halo, preferably Cl or F; Hal$_3$C—, Hal$_2$CH—, HalCH$_2$—, Hal$_3$CO—, Hal$_2$CHO or Hal CH$_2$O, wherein Hal represents halo (preferably F); R$^g$CH$_2$O—, R$^h$C(O)N(R)—, R$^h$SO$_2$N(R)— or R$^g$—R$^h$N—, wherein R$^g$ and R$^h$ independently represent hydrogen or C$_1$ to C$_8$ alkyl (preferably methyl or C$_2$ to C$_6$ alkyl or C$_2$ to C$_4$ alkyl), or R$^g$—R$^h$N— represents an optionally substituted C$_3$ to C$_8$, preferably C$_3$ to C$_6$, heterocyclic ring optionally containing from 1 to 3 further heteroatoms independently selected from O, N and S; hydrogen; or R$^k$C(O)O— or R$^k$C(O)—, R$^k$ representing hydrogen, optionally substituted phenyl or C$_1$ to C$_6$ alkyl (preferably methyl, ethyl, iso-propyl or tert-butyl). For optional substitution of the heterocyclic ring represented by R$^g$—R$^h$N—, at least one (eg, one, two or three) substituents may be provided independently selected from C$_1$ to C$_6$ alkyl (eg, C$_2$ to C$_4$ alkyl, more preferably methyl); phenyl; CF$_3$O—; F$_2$CHO—; C$_1$ to C$_8$ alkoxy, preferably methoxy, ethoxy or C$_3$ to C$_6$ alkoxy; C$_1$ to C$_8$ alkoxyC(O), preferably methoxycarbonyl, ethoxycarbonyl, tert-butoxycarbonyl or C$_3$ to C$_6$ alkoxyC(O)—; phenoxycarbonyl; phenoxy; C$_1$ to C$_8$ alkanoyl, preferably acetyl, ethanoyl or C$_3$ to C$_6$ alkyanoyl; carboxy; C$_1$ to C$_8$ alkylS(O)$_{nn}$ wherein nn is an integer between 0 and 2, preferably methylthio, ethylthio, C$_3$ to C$_6$ alkylthio, methylsulphinyl, ethylsulphinyl, C$_3$ to C$_6$ alkylsulphinyl, methylsulphonyl, ethylsulphonyl or C$_3$ to C$_6$ alkylsulphonyl; hydroxy; halo (eg, F, Cl or Br); R$^m$R$^n$N— where R$^m$ and R$^n$ are independently hydrogen or C$_1$ to C$_6$ alkyl (preferably C$_2$ to C$_4$ alkyl, more preferably methyl, most preferably R$^m$=R$^n$=methyl); and nitro.

Where optional substitution of a ring is mentioned at various places, this most preferably refers to one, two, three or more substituents selected from C$_1$ to C$_8$ alkyl (eg, C$_2$ to C$_6$ alkyl, and most preferably methyl); C$_1$ to C$_8$ alkoxy, preferably methoxy, ethoxy or C$_3$ to C$_6$ alkoxy; C$_1$ to C$_8$ alkylS(O)$_{nn}$ wherein nn is an integer between 0 and 2, preferably methylthio, ethylthio, C$_3$ to C$_6$ alkylthio, methylsulphinyl, ethylsulphinyl, C$_3$ to C$_6$ alkylsulphinyl, methylsulphonyl, ethylsulphonyl or C$_3$ to C$_6$ alkylsulphonyl; halo (eg, F, Cl or Br); CN; and NO$_2$.

Preferred optional substituents on A when A is C$_1$ to C$_8$ alkyl include: optionally-substituted phenyl or an optionally substituted 3- to 8-membered heterocyclic ring containing from 1 to 4 heteroatoms independently selected from O, N and S.

Preferred optional substituents when the structure N—A (—R$^4$) represents a 3- to 8-membered heterocyclic ring include: C$_1$ to C$_4$ alkyl, N-(C$_1$ to C$_4$ alkyl)amino, N,N-di-(C$_1$ to C$_4$ alkyl)amino, CN, halo, carbamoyl, NHC(O)—R$^p$, C(O)NH—R$^p$, NHS(O)$_{nn}$R$^p$, C$_1$ to C$_4$ alkylS(O)$_{nn}$; wherein nn and mm independently represent an integer between 0 and 2. and R$^p$ is C$_1$ to C$_4$ alkyl.

Preferred optional substituents on A when the optional substituents is a 3- to 8-membered heterocyclic ring include optionally substituted pyridyl, thienyl, piperidinyl, imidazolyl, triazolyl, thiazolyl, pyrrolidinyl, piperazinyl, morpholinyl or imidazolinyl. Further preferred optional substituents include pyridyl, or a group of formula XIV, XV, XVI, XVII, XVIII, XIX or XX:

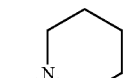

XIV

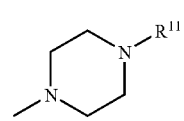

XV

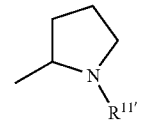

XVI

-continued

XVII 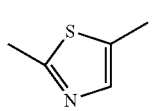

XVIII 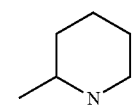

XIX 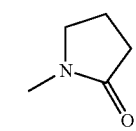

XX 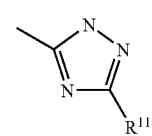

wherein
$R^{11}$ represents hydrogen; optionally substituted $C_1$ to $C_8$ alkyl (preferably, $C_1$ to $C_6$ alkyl, eg, methyl, ethyl or tert-butyl); hydroxy; halo (eg, F, Cl or Br); CN; $C_1$ to $C_8$ alkoxy (preferably, $C_1$ to $C_6$ alkoxy, eg, methoxy or ethoxy); or $CF_3$; and
$R^{11'}$ represents hydrogen or optionally substituted $C_1$ to $C_8$ alkyl (preferably, $C_1$ to $C_6$ alkyl, eg, methyl).

A preferred group of compounds of the invention comprises a compound of formula Ia:

formula Ia
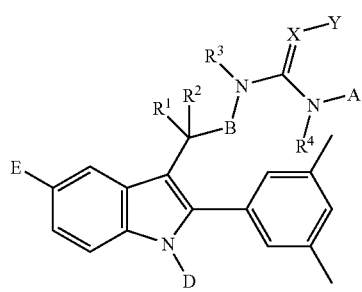

wherein:
E is selected from a II, III or VIII:

II 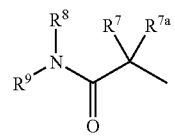

III 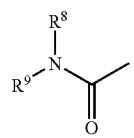

VIII 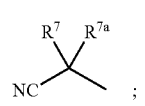

and A, B, D, X, Y, $R^1$, $R^2$, $R^3$, $R^4$, $R^7$, $R^{7a}$, $R^8$ and $R^9$ are as defined above; or a salt, pro-drug or solvate thereof.

A further preferred group of compounds of the invention comprises a compound of formula Ib:

formula Ib
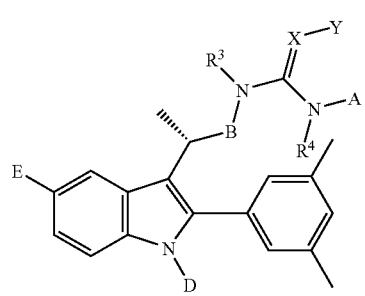

wherein:
E is selected from a group of formula II, III or VIII:

II 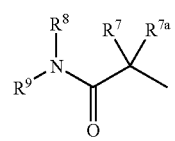

III 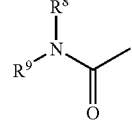

VIII 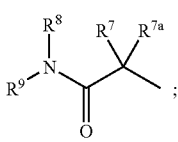

and A, B, D, X, Y, $R^3$, $R^4$, $R^7$, $R^{7a}$, $R^1$ and $R^9$ are as defined above; or a salt, pro-drug or solvate thereof.

A yet further preferred group of compounds of the invention comprises a compound of formula Ia or Ib wherein:
E is a group of formula II:

II $NR^8(-R^9)$ represents an optionally substituted 7- to 8-membered bicyclic heterocyclic ring and A, B, D, X, Y, $R^3$, $R^4$, $R^7$, $R^{7a}$, $R^8$ and $R^9$ are as defined above; or a salt, pro-drug or solvate thereof.

Particularly preferred compounds according to the present invention are wherein the compound is selected from a compound of formula XXI to XXXI:—
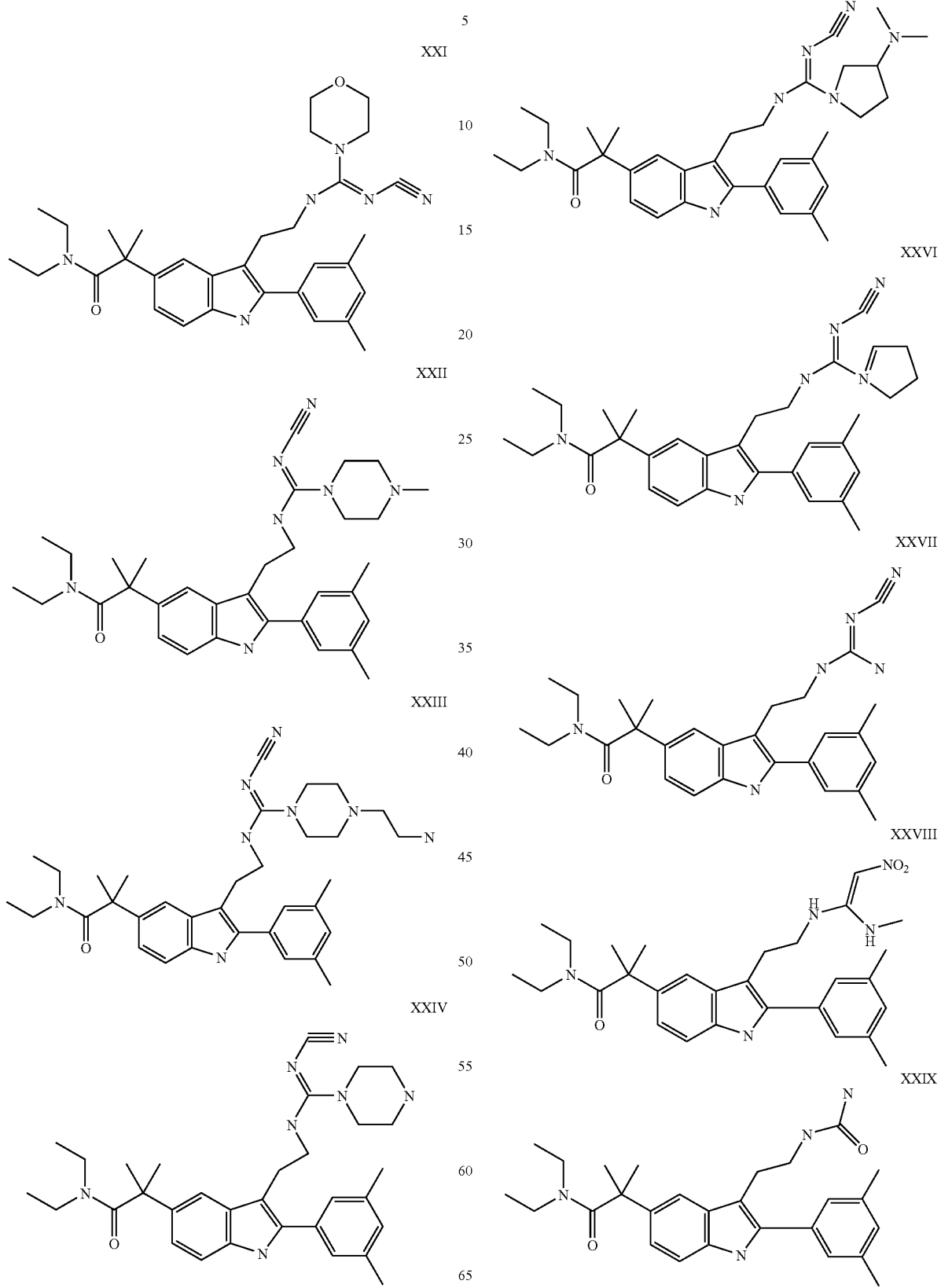

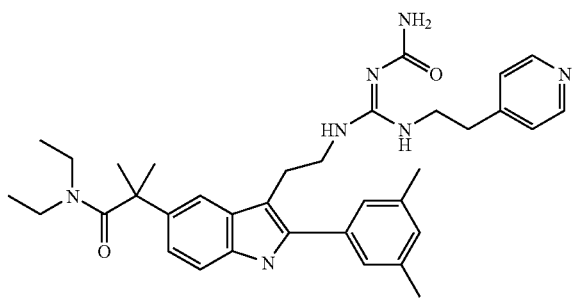

XXX

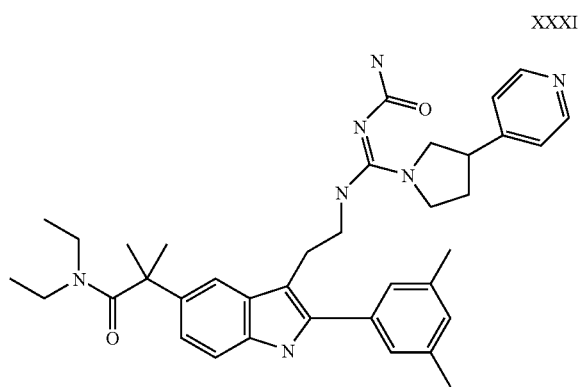

XXXI

It is to be understood that, insofar as certain of the compounds of the invention may exist in optically active or racemic forms by virtue of one or more asymmetric carbon atoms, the invention includes in its definition any such optically active or racemic form which possesses the property of antagonizing gonadotropin releasing hormone (GnRH) activity. The synthesis of optically active forms may be carried out by standard techniques of organic chemistry well known in the art, for example by synthesis from optically active starting materials or by resolution of a racemic form. Similarly, activity of these compounds may be evaluated using the standard laboratory techniques referred to hereinafter.

The invention also relates to any and all tautomeric forms of the compounds of the different features of the invention that possess the property of antagonizing gonadotropin releasing hormone (GnRH) activity.

It will also be understood that certain compounds of the present invention may exist in solvated, for example hydrated, as well as unsolvated forms. It is to be understood that the present invention encompasses all such solvated forms which possess the property of antagonizing gonadotropin releasing hormone (GnRH) activity.

The compounds of Formula I may be administered in the form of a pro-drug which is broken down in the human or animal body to give a compound of the Formula I. Examples of pro-drugs include in-vivo hydrolysable esters of a compound of the Formula I. Various forms of pro-drugs are known in the art. For examples of such pro-drug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

An in-vivo hydrolysable ester of a compound of the Formula I containing a carboxy or a hydroxy group is, for example, a pharmaceutically-acceptable ester which is hydrolysed in the human or animal body to produce the parent acid or alcohol. Suitable pharmaceutically-acceptable esters for carboxy include $C_1$ to $C_6$alkoxymethyl esters for example methoxymethyl, $C_1$ to $_6$alkanoyloxymethyl esters for example pivaloyloxymethyl, phthalidyl esters, $C_3$ to $C_8$cycloalkoxycarbonyloxy $C_1$ to $C_6$alkyl esters for example 1-cyclohexylcarbonyloxyethyl; 1,3-dioxolen-2-onylmethyl esters, for example 5-methyl-1,3-dioxolen-2-onylmethyl; and $C_1$ to $C_6$alkoxycarbonyloxyethyl esters.

An in-vivo hydrolysable ester of a compound of the Formula I containing a hydroxy group includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxy-methoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A suitable pharmaceutically-acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of formula I can be prepared by a process comprising a step selected from (a) to (e) as follows, these processes are provided as a further feature of the invention:—

(a) Reaction of a compound of formula XXXII as follows

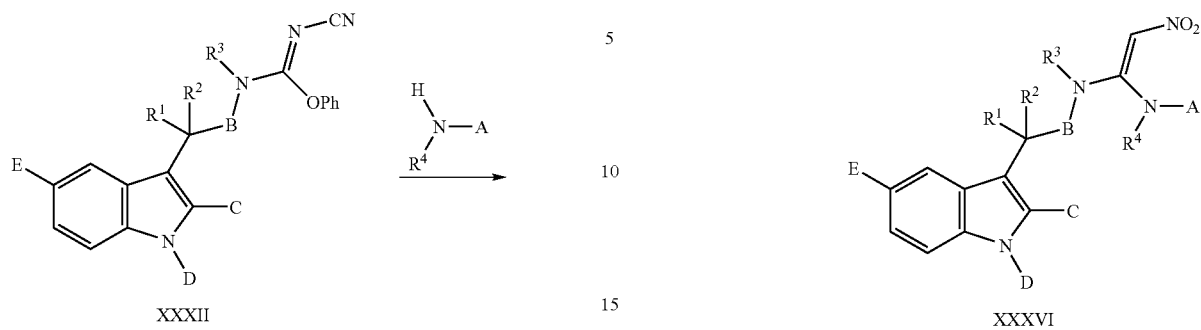

XXXII

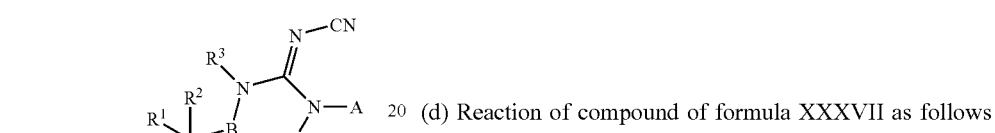

XXXIII (b) Cleavage of the CN group of compound of formula XXXIII in the presence of acid to produce compound of formula XXXIV

XXXIV

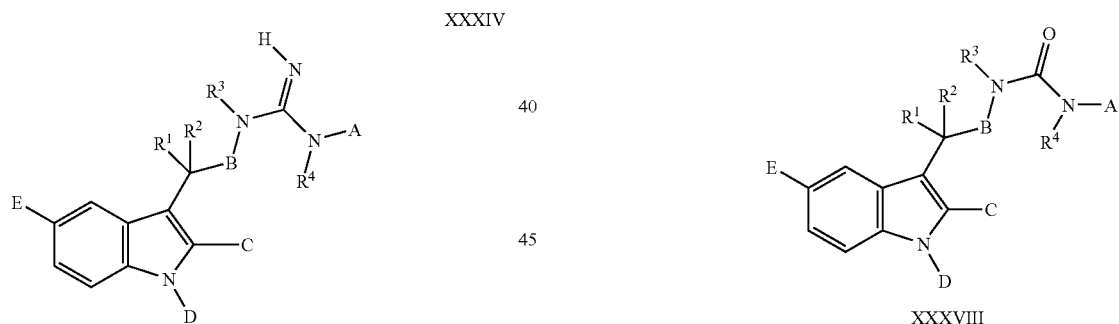

(c) Reaction of compound of formula XXXV as follows

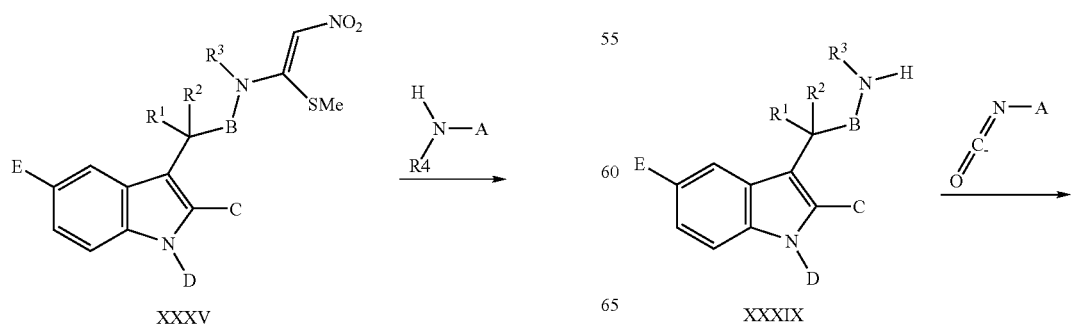

XXXV

-continued

XXXVI (d) Reaction of compound of formula XXXVII as follows

XXXVII

XXXVIII (e) Reaction of compound of formula XXXIX as follows

XXXIX

19

-continued

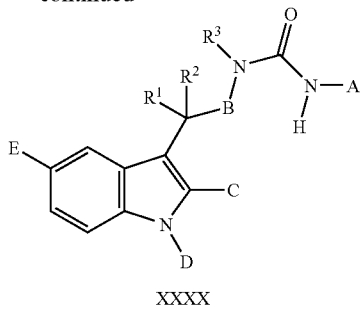

XXXX and thereafter if necessary:

i) converting a compound of the formula I into another compound of the formula I;

ii) removing any protecting groups;

iii) forming a salt, pro-drug or solvate.

It will be appreciated by those skilled in the art that in the processes of the present invention certain functional groups such as hydroxyl or amino groups in the starting reagents or intermediate compounds may need to be protected by protecting groups. Thus, the preparation of the compounds of formula I may involve, at an appropriate stage, the addition and subsequent removal of one or more protecting groups.

The protection and de-protection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The de-protection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The de-protection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such

20 as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

EXPERIMENTAL

General Reaction Schemes

In the following schemes wherein Ri, Rii and Riii represent optional substituents on the phenyl ring which are optionally protected as necessary and R represents a protecting group, group C has been depicted as substituted phenyl for illustration purposes only. Other definitions of C are also appropriate.

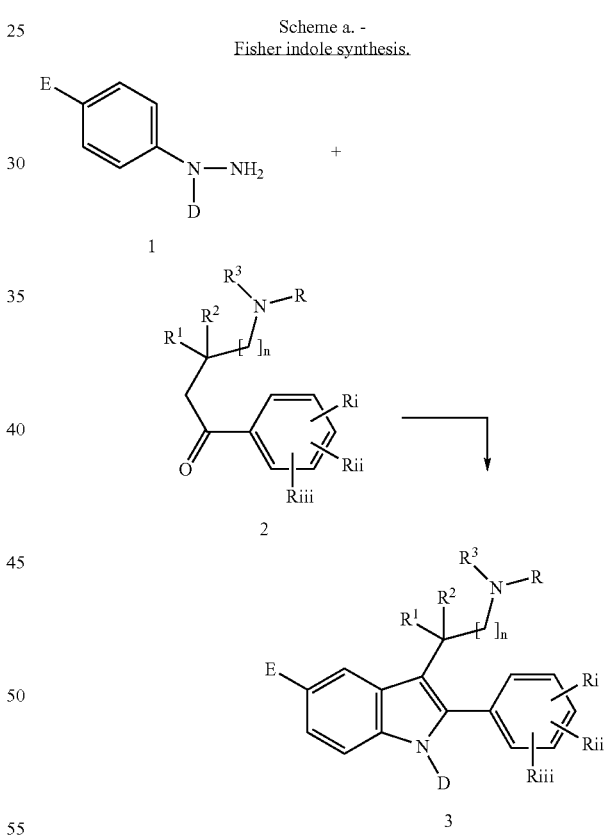

Tryptamines, such as 3 can be synthesised by the classic Fisher indole synthesis reaction by the condensation of a hydrazine 1 and a ketone 2, bearing hydrogen atoms α to the carbonyl (Scheme a). Treatment of these reactants in a suitable solvent, such as acetic acid, ethanol, tert-butanol, toluene, in the presence of an acid, such as sulphuric, hydrochloric, polyphosphoric and/or a Lewis acid, for example, boron trifluoride, zinc chloride, magnesium bromide, at elevated temperatures (for example 100° C.), gives the desired product. R represents a protecting group, eg tert-butylcarbamate or phthalimide.

Scheme b

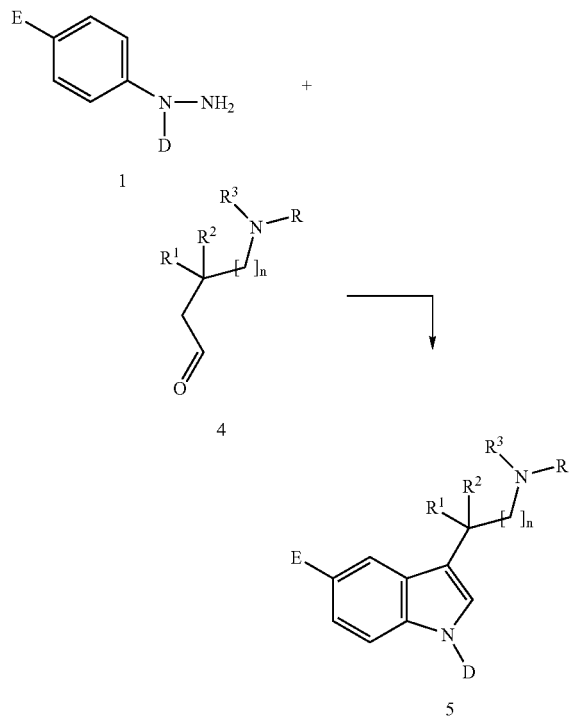

Tryptamines, such as represented in structure 5, can also be made using aldehydes 4, bearing hydrogen atoms α to the carbonyl, by cyclization using the conditions above. In this case the substituent at the 2-position must be added later (see scheme d).

Scheme c

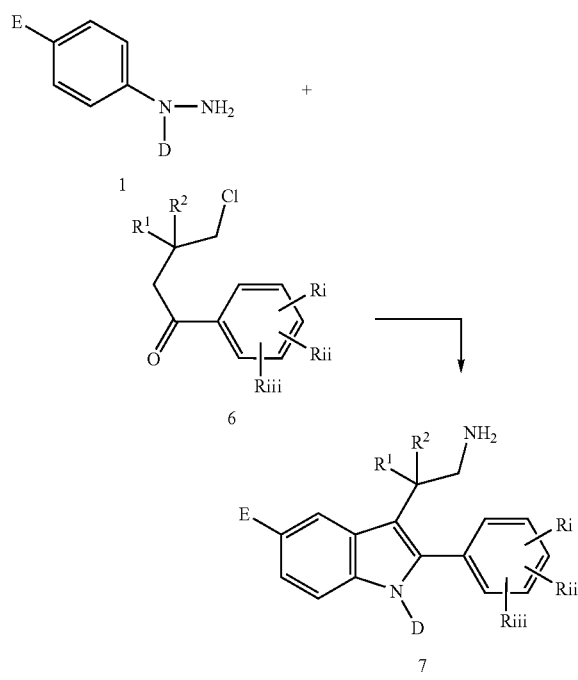

Tryptamine may also be synthesised utilising the Granburg reaction, wherein a hyradazine 1 is mixed with ketone 6, bearing a chlorine atom γ to the carbonyl, and heated in a suitable solvent such as ethanol, tert-butanol, toluene at a temperature between 50° C. and 120° C. (Scheme c).

Scheme d

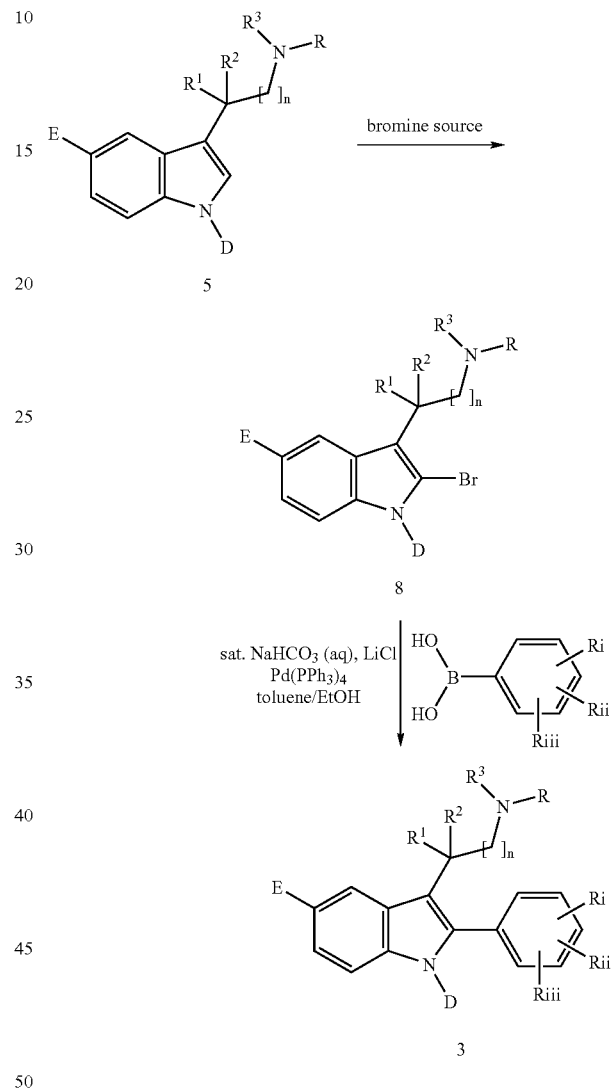

The tryptamine 5 can be treated with a 'bromine source', such as molecular bromide, pyridinium tribromide, pyrrolidone hydrobromide or polymer supported reagent equivalents, in an inert solvent such as chloroform, methylene chloride at −10° C. to 25° C. to yield the 2-bromo compound 8 (Scheme d). Reaction under Suzuki conditions with a palladium(0) catalyst, a weak base such aqueous sodium carbonate or saturated sodium hydrogen carbonate and the like, and a substituted aryl boronic acid from commercial sources or prepared (as described in: Gronowitz, S.; Homfeldt, A. -B.; Yang, Y., -H Chem. Sci. 1986, 26, 311-314), in an inert solvent such as toluene, benzene, dioxane, THF, DMF and the like, with heating between 25° C. and 100° C., preferably 80° C., for a period of 1-12 hours, to give the desired compound 3.

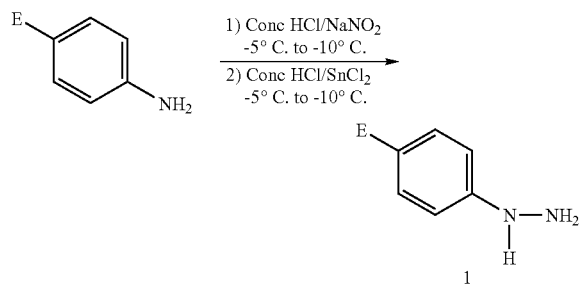

The hydrazines 1 can be purchased from commercial sources either as a free base or suitable salt (e.g. hydrochloride), which are both acceptable under the reaction conditions. Hydrazines may be synthesised by the two-step process of diazotisation of an aniline, under the preferred conditions of concentrated hydrochloric acid sodium nitrite at a temperature between −10° C. and −5° C., then reduction under the preferred conditions of tin(II) chloride in concentrated hydrochloric acid at a temperature between −10° C. and −5° C.

Scheme e.

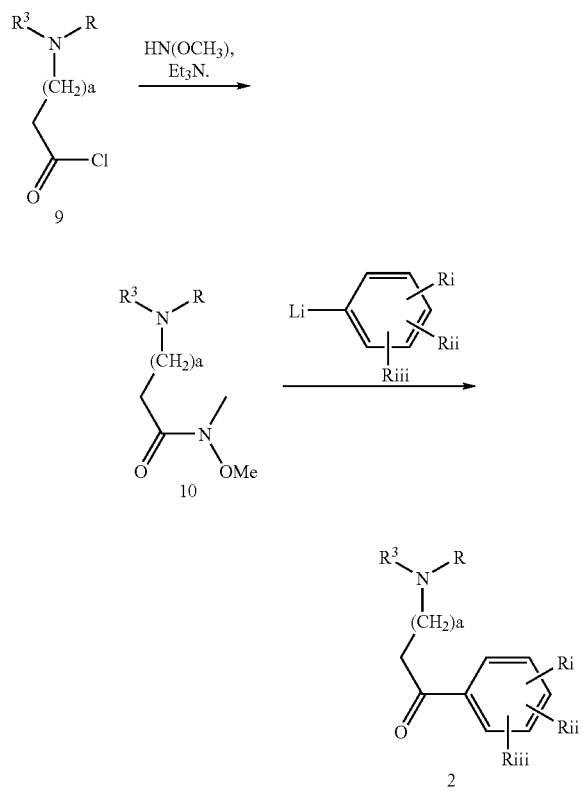

Substituted ketones 2 can be prepared, as outlined in Scheme e starting from appropriate acid chlorides such as 9. Treatment of the acid chloride with N,N-dimethylhydroxylamine hydrochloride in the presence of an amine base such as triethylamine, and a suitable solvent such as methylene chloride at a temperature of −10° C. to 25° C., yields the amide 10. Further reaction with a substituted aryl organolithium (prepared essentially as described in Wakefield B, J.; *Organolithium Methods* Academic Press Limited, 1988, pp. 27-29 and references therein) in an inert solvent such as tetrahydrofuran, diethyl ether, benzene, toluene or mixture thereof and the like, at a temperature between −100° C. and 0° C. then quenching of the reaction mixture with a mineral acid such as hydrochloric acid, yields the aryl ketone 2.

Scheme f.

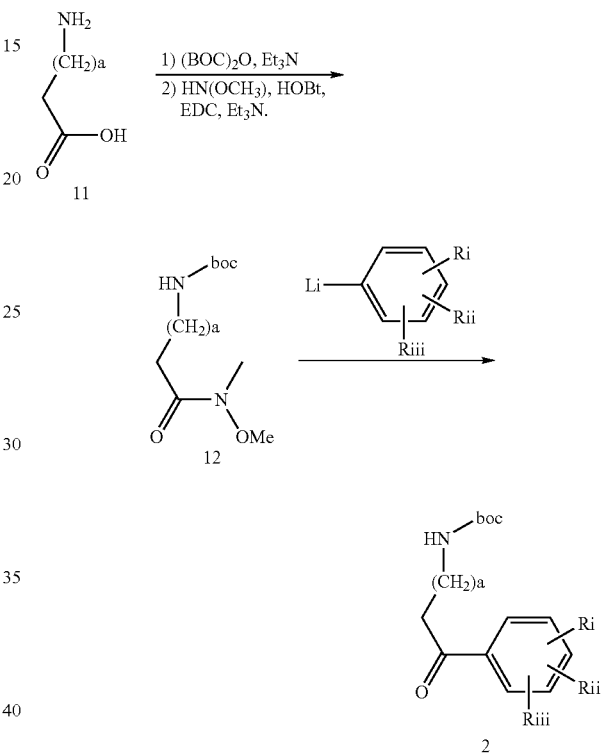

Commencing with a readily available amino acid with a suitable chain length [a] 11, the nitrogen atom can be brought in at the beginning of the synthesis by the route shown in Scheme f. Protection of the amine group of 11 with a tert-butylcarbamate group is achieved by condensation with di-tert-butyl di-carbonate in the presence of an amine base, for example triethylamine, in an inert solvent such as methylene chloride, chloroform, benzene, toluene, tetrahydrofuran and mixtures thereof and the like, at a temperature of −10° C. to 25° C. Coupling of the acid product with N,N-dimethylhydroxylamine in the presence of a coupling reagent 1-(3-dimethylaminopropyl)-3-ethylcarbodiimide hydrochloride (EDC) or 1,3-dicyclohexylcarbodiimide (DCC) or the like, with or without 1-hydroxybenotriazole (HOBt), and suitable amine base, such as triethylamine and the like, in an inert solvent such as methylene chloride, chloroform, dimethylformamide, or mixture thereof, at or near room temperature for a period of 3 to 24 hours provided the corresponding coupled product 12. Following the same route described above for scheme d, the aryl group can then be installed.

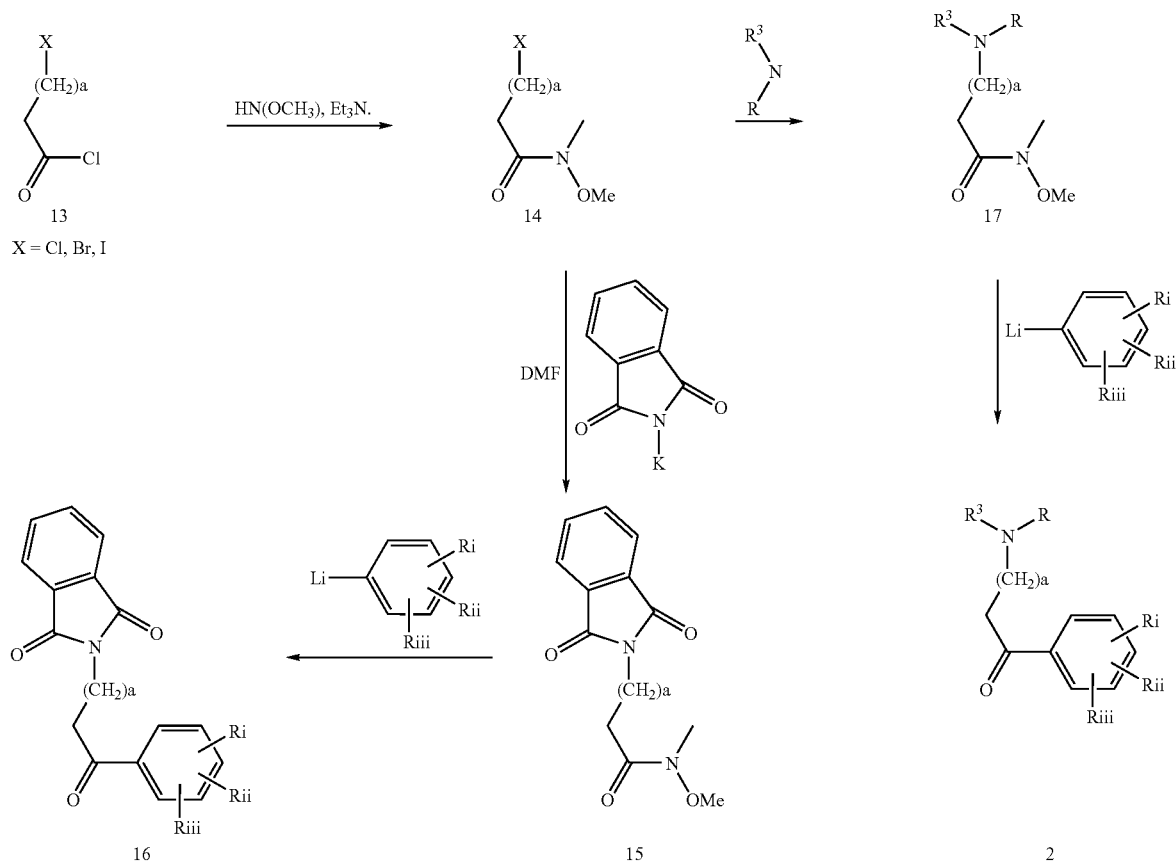

Scheme g illustrates another method for the synthesis of ketone such as 2 and 16, where the nitrogen group is introduced at a latter stage. As above a Weinreb amide 14 can be synthesised from an acid chloride. Treatment with the required amine, in an inert solvent such as THF, toluene, water and the such like can displace the group X to give 17. As above the aryl group can be introduced by displacement of the Weinreb amide with a suitable aryl lithium nucleophile. Alternatively the nitrogen atom can be introduced already protected as a phthalimide by displacement of the group x by potassium phthalimide, or similar salt thereof, by heating in an inert polar solvent such as DMF, DMSO, THF, toluene with or without the presence of a catalyst such as tetrabutylammonium iodide and the such like, to yield the compound 15. Again displacement of the Weinreb amide with an organolithium species completes the synthesis of a ketone suitable for cyclization under the Fischer condition described above for indole synthesis.

Scheme h.

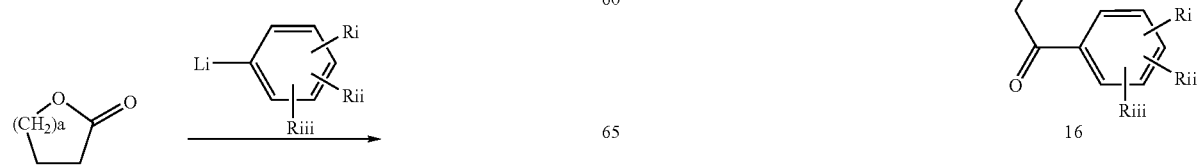

-continued

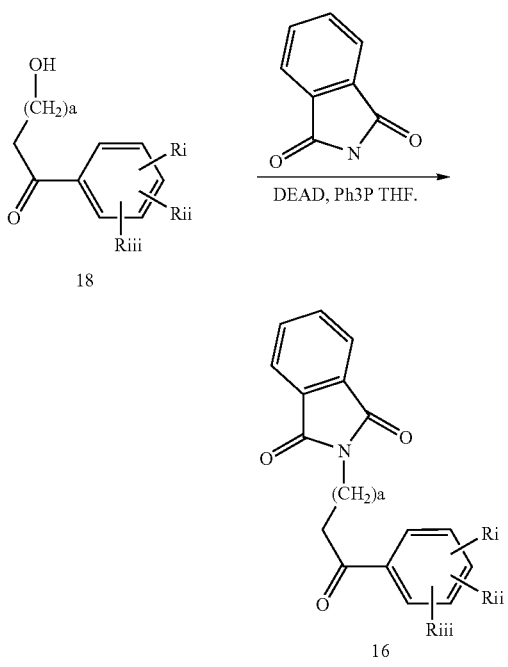

An alternative approach to a phthalimide protected nitrogen ketone, such as 16, can be taken by firstly treating a lactone, with an organolithium species as in the above schemes in a suitable solvent such as THF or ether at a low temperature of between −100° C. and −50° C. to yield a primary alcohol 18 (Scheme h). The hydroxyl function of 18 is replaced with a phthalimide group by a Mitsunobu reaction with an activating agent such as diethyldiazocarboxylate (DEAD), diisopropyldiazocarboxylate or the like with triphenylphosphine, tri-butylphosphine and the like, in an inert solvent such as benzene, toluene, tetrahydrofuran or mixtures thereof to give the desired ketone 16.

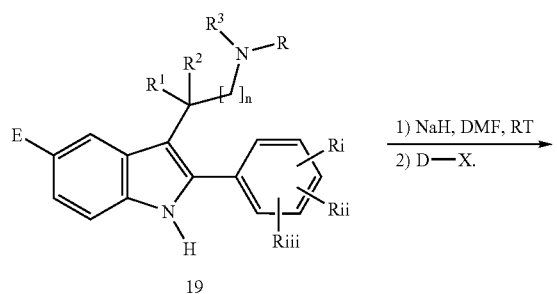

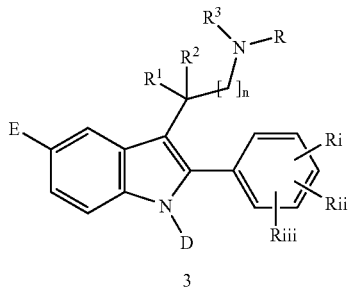

If the group D was not present on the starting hydrazine before cyclization to form an indole it may be added post cyclization by an alkylation reaction (19→3). The indole is de-protonated by a strong base, such as sodium hydride, n-butyl lithium, lithium diisopropylamine, sodium hydroxide, potassium tert-butoxide in a suitable inert solvent such as THF, DMF, DMSO and the such like, and an alkyl halide added and the mixture stirred at room temperature.

Scheme i

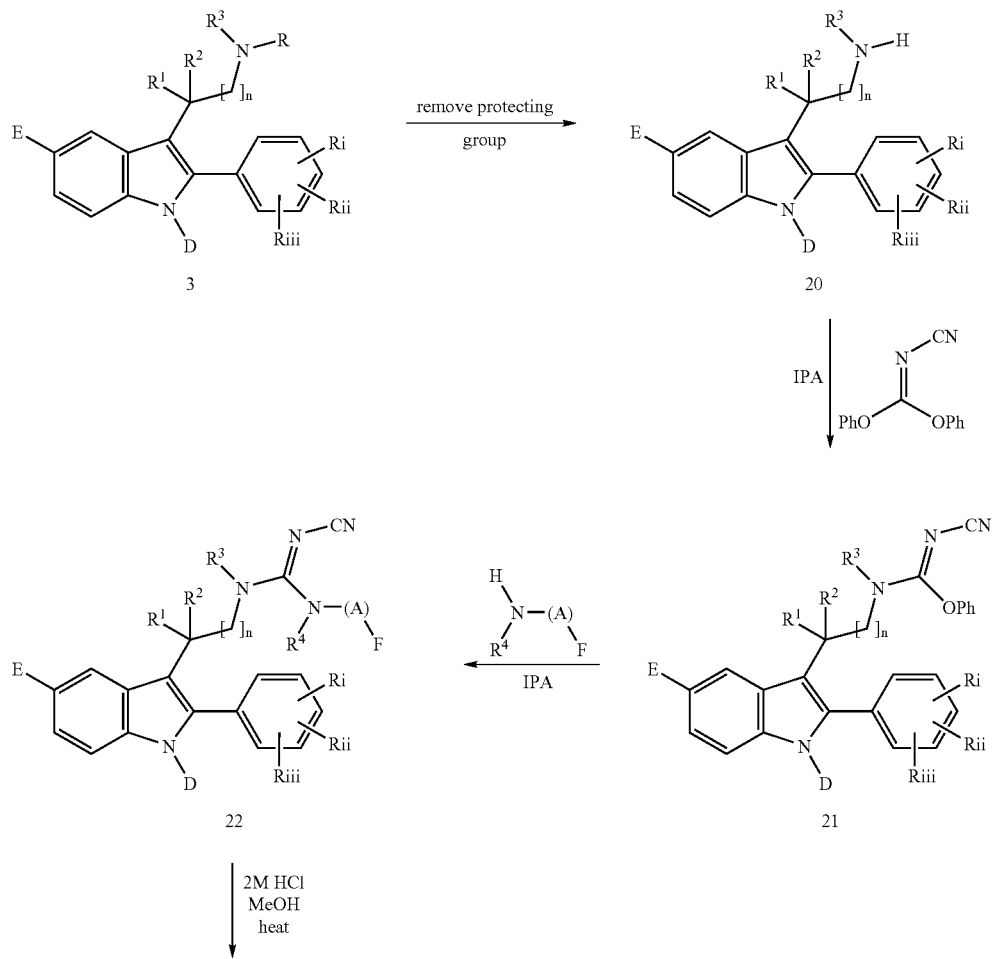

-continued

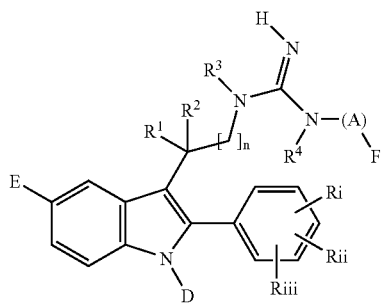

23

Depending on the route used above a tryptamine 20 suitable for conversion to a cyano-guandine can be formed by removal of the protecting group, for example if a tert-butylcarbamate group was used then removal is accomplished using a strong acid, for example trifluoroacetic acid or hydrochloric acid in an inert solvent such as methylene chloride, chloroform, THF or dioxane at a temperature between −20° C. and 25° C. A phthalimide group, for example, can be removed by hydrazine in a suitable solvent for example methanol, ethanol, methylene chloride, chloroform, THF dioxane at a temperature between −20° C. and 25° C. The primary amine 20 can be converted to a cyano-guanidine 22 by the two step process of reaction with diphenyl cyanocarbonimidate in an inert organic solvent such as iso-propyl alcohol, methylene chloride, chloroform, benzene, tetrahydrofuran and the like, at a temperature between −20° C. and 50° C., followed by condensation with an appropriately substituted amine in an inert organic from the list above, with heating at a temperature between −20° C. and 100° C. (Scheme I 20→21→22). Further treatment of 22 with 2 molar Hydrochloric acid in methanol at elevated temperature yields guanidine compounds 23.

Scheme j.

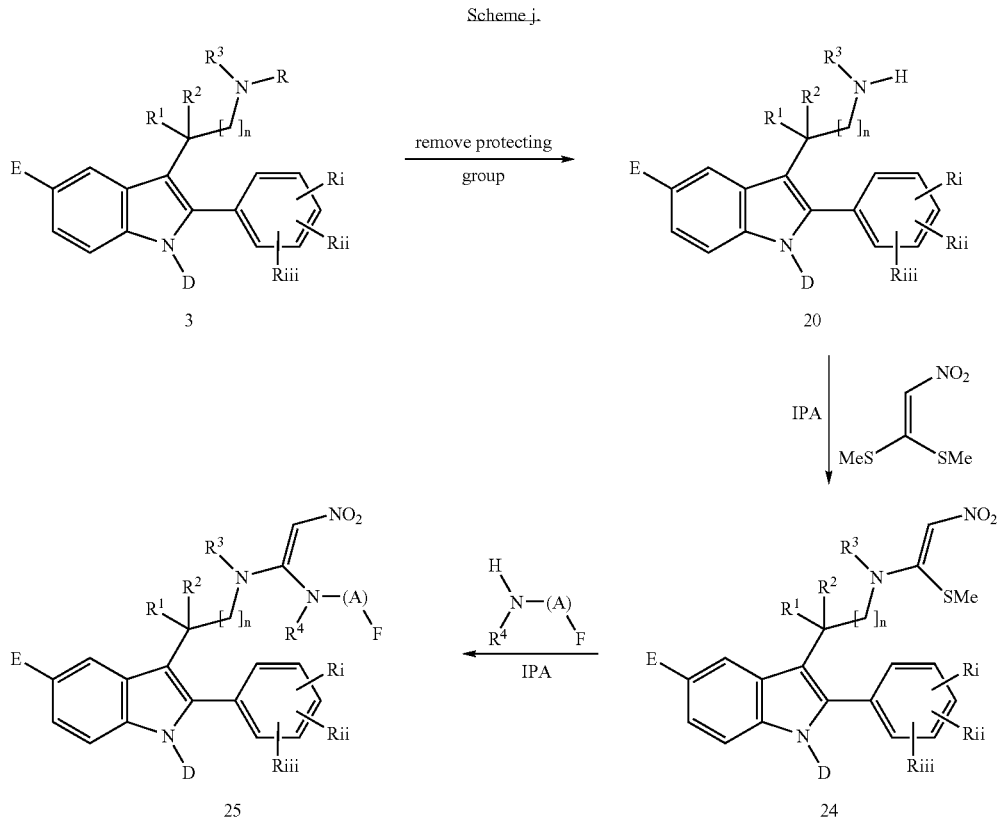

Similarly, reaction with 1,1'-bis(methylthio)-2-nitroethylene in an inert solvent such methylene chloride, chloroform, benzene, tetrahydrofuran and the like, followed by condensation with an appropriately substituted amine in an inert organic solvent from the list above yields the nitroethylene-imidazo[1,2-a]pyridine 25 (Scheme j, 20→24→25).

Scheme k.

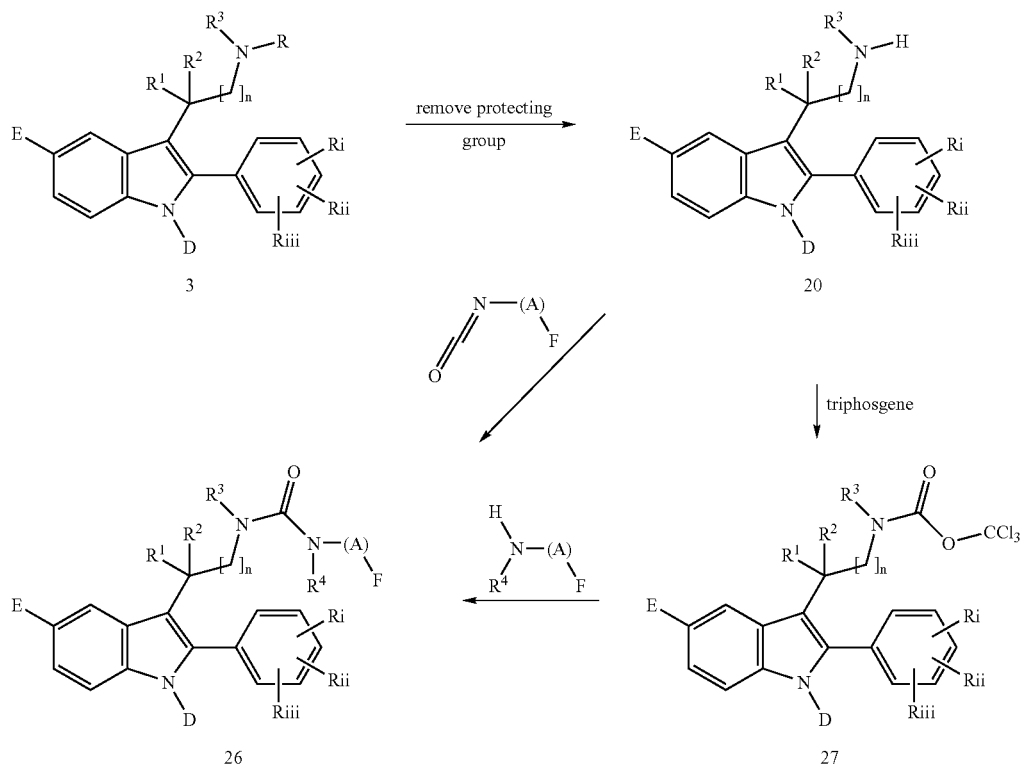

Again in a similar fashion the suitable tryptamine 20, derived from de-protection, can be converted to a urea by either direct treatment with an iso-cyanate in an inert solvent such as methylene chloride, chloroform or THF and the such like, or by a two step procedure of reaction with triphosgene (20→27) followed by addition of an amine (27→26), bearing the required substitution to yield 26.

EXAMPLES

The invention will now be illustrated with the following non-limiting Examples in which, unless otherwise stated:

(i) evaporations were carried out by rotary evaporation in vacuo and work-up procedures were carried out after removal of residual solids such as drying agents by filtration;

(ii) operations were carried out at room temperature, that is in the range 18-25° C. and under an atmosphere of an inert gas such as argon or nitrogen;

(iii) yields are given for illustration only and are not necessarily the maximum attainable;

(iv) the structures of the end-products of the Formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

(vi) chromatography was performed on silica (Merck Keiselgel: Art.9385);

(vii) isolute™ refers to silica (SiO$_2$) based columns with irregular particles with an average size of 50 μm with nominal 60 Å porosity [Source: Jones Chromatography, Ltd., Glamorgan, Wales, United Kingdom].

Abbreviations

| | |
|---|---|
| brine | a saturated solution of sodium chloride in distilled water |
| DCC | 1,3-dicyclohexylcarbodiimide |
| DEAD | diethyldiazocarboxylate |
| DMSO | Dimethyl sulphoxide |
| DMF | dimethylformamide |
| EDC | 1-(3-dimethylaminopropyl)-3-ethylcarbodiimide hydrochloride |
| HOBt | 1-hydroxybenotriazole |
| IPA | isopropyl alcohol |
| RM | reaction mixture |
| RT | room temperature |
| THF | tetrahydrofuran |

Example 1

| STRUCTURE | EXAMPLE |
|---|---|
| 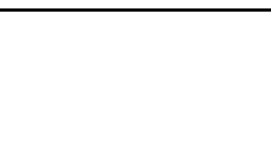 | 1.01 |

Synthesis of this compound is described with reference to Scheme 1 below.

Morpholine (260 mg, 3 mmol) was added to a stirred suspension of L (0.18 mmol) in IPA (2 ml) and the mixture heated at reflux for 36 hours. The RM was concentrated in vacuo and the residues purified by chromatography on $SiO_2$ eluting with 5% $MeOH/CH_2Cl_2$ to give 1.01 as an off-white foam white 43.5 mg (46%).

$^1$H NMR (300 MHz, $CDCl_3$) 0.60-0.80 (m,3H); 1.00-1.20 (m,3H); 1.60 (s,6H); 2.4 (s,6H); 2.80-3.00 (m,2H); 3.08-3.14 (m,4H); 3.2-3.3 (t,2H); 3.3-3.42 (m, 2H); 3.5-3.58 (m,4H); 3.62-3.72 (m,2H); 4.5-4.6 (m,1H); 7.03 (s,1H); 7.05-7.13 (m,1H); 7.20 (s,2H); 7.2-7.36 (m,1H); 7.42 (s,1H); 8.15 (s,1H).

MS ($ES^+$) m/z $(M+H)^+$ 543.39
MS ($ES^-$) m/z $(M-H)^-$ 541.33

Following a procedure similar to that described in Example 1, the following compounds were prepared.

| STRUCTURE | EXAMPLE | MS (ES)+ |
|---|---|---|
| 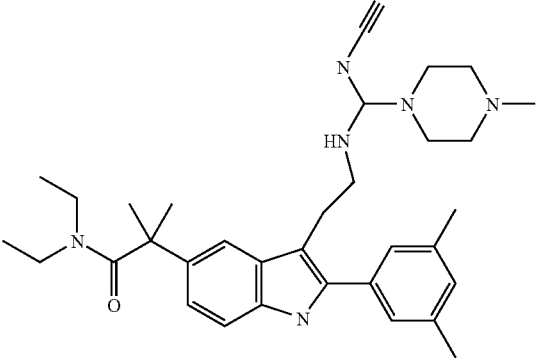 | 1.02 | 556.74 (M + H)+ |
| 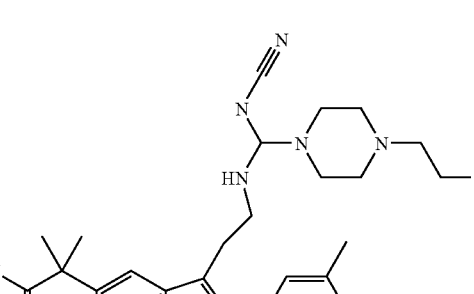 | 1.03 | 585.55 (M + H)+ |

-continued

| STRUCTURE | EXAMPLE | MS (ES)+ |
|---|---|---|
| (structure) | 1.04 | 542.54 (M + H)+ |
| (structure) | 1.05 | 570.51 (M + H)+ |
| (structure) | 1.06 | 527.48 (M + H)+ |
| (structure) | 1.07 | 473.48 (M + H)+ |

Example 2

| STRUCTURE | EXAMPLE |
|---|---|
| 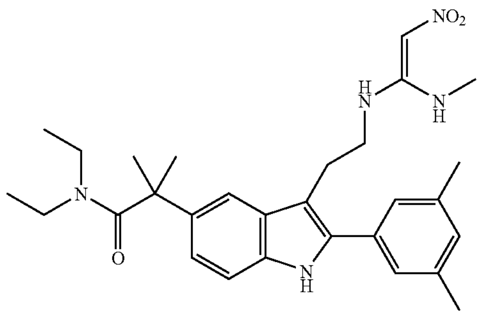 | 2 |

Synthesis of this compound is described with reference to Scheme 2 below.

Methylamine (1 ml, 2.00 mmol) was added to a stirred suspension of M (46.4 mg, 0.089 mmol) in $CH_2Cl_2$ (2 ml) and the mixture stirred for 60 hrs. The RM was concentrated in vacuo and the residues purified by chromatography on $SiO_2$ (Isolute, 10 g), eluting with a gradient 0-10% MeOH/ $CH_2Cl_2$ to give 2.01 as a white solid 31.3 mg (70%).

$^1$H NMR (300 MHz, $CDCl_3$) 0.6-0.8 (m,3H); 1.0-1.2 (m,3H); 1.6 (s,6H); 2.35 (s,6H); 2.40-2.60 (m,3H); 2.8-3.0 (m,2H); 3.00-3.60 (m, 6H); 4.4-4.9 (m,1H); 6.2-6.6 (m,1H); 7.02 (s,1H); 7.1 (d,1H); 7.15 (bs,2H); 7.3-7.45 (m,2H); 8.45 (s,1H); 9.80-10.2 (bm,1H).

MS (ES$^+$) m/z (M+H)$^+$ 506.63
MS (ES$^-$) m/z (M−H)$^-$ 504.64

Example 3

| STRUCTURE | EXAMPLE |
|---|---|
| 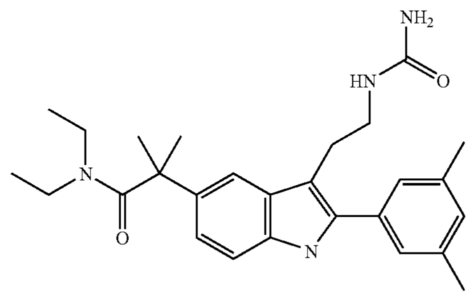 | 3 |

Synthesis of this compound is described with reference to Scheme 3 below.

A solution of K (100 mg, 0.25 mmol) in MeOH (5 mL) was treated with 2N HCl (2 mL) followed Potassium cyanate (405 mg, 5 mmol). The mixture was stirred for 18 hrs then quenched with saturated $NaHCO_3$ (aq) (100 mL) and extracted with EtOAc (3×50 mL). The combined organics were washed with brine (2×50 mL), dried over $MgSO_4$, filtered and evaporated. The crudes were purified by chromatography on $SiO_2$ eluting with a gradient 0-5% MeOH/ $CH_2Cl_2$ to give 3 as an off-white foam 82.0 mg (73%).

$^1$H NMR (300 MHz, $CDCl_3$) 0.60-0.80 (m,3H); 1.00-1.20 (m,3H); 1.60 (s,6H); 2.18 (s,6H); 2.84-3.00 (m,2H); 3.06-4.00 (m, 6H); 4.24 (s,2H); 4.66-4.72 (m,1H); 7.00-7.1 (m,2H); 7.2 (s,2H); 7.3-7.34 (m,1H); 7.46 (s,1H); 8.12 (s,1H).

MS (ES$^+$) m/z (M+H)$^+$ 449.57
MS (ES$^-$) m/z (M−H)$^-$ 447.59

Example 4

| STRUCTURE | EXAMPLE |
|---|---|
| 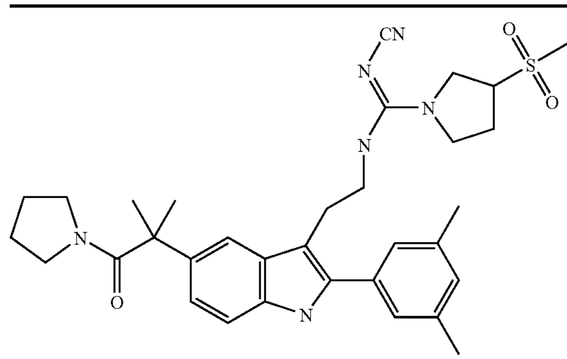 | 4 |

Synthesis of this compound is described with reference to Scheme 4 below.

3-(Methylsulphonyl) pyrrolidine (746 mg, 5 mmol) was added to a stirred suspension of Q (547 mg, 1 mmol) in IPA (10 mL) and the mixture heated at reflux for 18 hrs. The RM was concentrated in vacuo and the residues purified by chromatography on SiO$_2$ (Isolute, 50 g), eluting with a gradient 0-10% MeOH/CH$_2$Cl$_2$ to give 4 as a white foam 393 mg (65.3%).

$^1$H NMR (300 MHz, CDCl$_3$) 1.4-1.8 (m,10H+H$_2$O); 2.1-2.3 (m,1H); 2.3-2.5 (m,7H); 2.8(t,2H); 2.9 (s,3H); 3.1-3.45 (m, 4H); 3.45-3.9 (m,7H); 4.45 (t,1H); 7.02 (s,1H); 7.1 (dd,1H); 7.2 (s,2H); 7.3 (d,1H); 7.45 (s,1H); 8.2 (s,1H).

MS (ES$^+$) m/z (M+H)$^+$ 603.16
MS (ES$^-$) m/z (M-H)$^-$ 601.12

Example 5 white foam which was triturated with Et$_2$O (10 mL), filtered and dried under high vacuum to give 5 as a white powder 99.4 mg (48%).

$^1$H NMR (300 MHz, DMSO-D$_6$+CD$_3$COOD) 0.50-0.80 (m,3H); 0.90-1.10 (m,3H); 1.45 (s,6H); 1.8-2.1 (m,1H); 2.2-2.4 (m,7H); 2.70-3.00 (m,2H); 3.00-3.30 (m,4H); 3.30-3.65 (m,6H); 3.65-3.85 (m,1H); 6.87 (d,1H); 6.95 (s,1H); 7.17(s, 2H); 7.20-7.35 (m,3H); 7.38 (s,1H); 8.50 (d,2H).

MS (ES$^+$) m/z (M+H)$^+$ 622.51.

Synthesis of R (See Scheme 7)

4-Pyrrolidin-3-yl pyridine (1.00 g, 6.76 mmol) was added to a stirred suspension of L (1.00 g, 1.80 mmol) [See Scheme 1] in IPA (5 ml) and the mixture heated at reflux for 36 hours. The RM was concentrated in vacuo and the residues purified by chromatography on SiO$_2$ (Isolute, 50 g), eluting with a gradient 0-10% MeOH/CH$_2$Cl$_2$ to give R as a white foam 672 mg (61%).

| STRUCTURE | EXAMPLE |
|---|---|
| 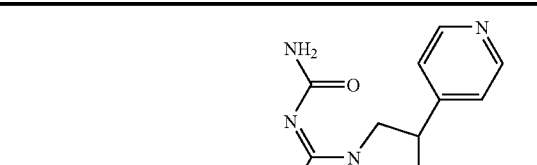 | 5.01 |

Synthesis of this compound is described with reference to Scheme 7 below.

2N HCl (5 mL) was added to a stirred solution of R (200 mg, 0.331 mmol) in dioxane (5 mL) and the resulting solution left to stir for 72 hours at room temperature. The reaction mixture was partitioned between saturated NaHCO$_3$ (100 mL) and EtOAc (4×50 mL). Combined organics were dried (MgSO$_4$), filtered and evaporated to a white foam. This was then purified by chromatography on SiO$_2$ (Varian, 10 g), eluting with a gradient 0-10% MeOH/CH$_2$Cl$_2$ to give a $^1$H NMR (300 MHz, CDCl$_3$) 0.60-0.80 (m,3H); 1.00-1.20 (m,3H); 1.60 (s,6H); 1.80-2.00(m,1H); 2.10-2.30 (m,1H); 2.35 (s,6H); 2.80-3.00 (m,2H); 3.10-3.50 (m, 8H); 3.60-3.80 (m,3H); 4.40 (m,1H); 6.97 (s,1H); 7.00-7.15 (m,3H); 7.20 (s,2H); 7.28-7.36 (m,1H); 7.41 (s,1H); 8.22 (s,1H); 8.48-8.60 (m,2H).

MS (ES$^+$) m/z (M+H)$^+$ 604.56
MS (ES$^-$) m/z (M-H)$^-$ 602.54

Following a procedure similar to that described in Example 5.01, the following compound was prepared.

| STRUCTURE | EXAMPLE | MS (ES)+ |
|---|---|---|
| 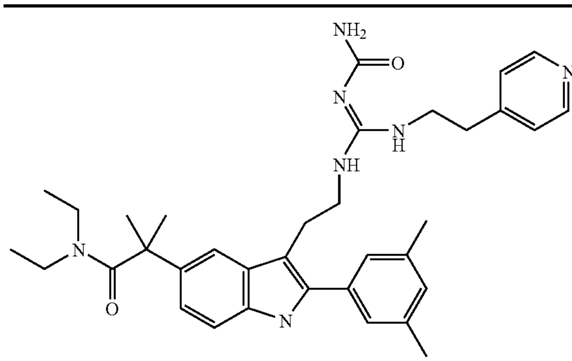 | 5.02 | 596.5 (M + H)+ |

Preparation of Starting Materials (1)

Syntheses for starting materials B, C, D, E and F used in the above examples are described with reference to Scheme 5 below.

2N NaOH (510 ml, 1.02 mol) was added to a stirred solution of A (48.5 g, 205 mmol) in MeOH (550 ml) and the resulting mixture heated at reflux for 2 hours. The RM was concentrated, acidified to pH 4 with 2N HCl and extracted with EtOAc (4×200 ml). The combined organics were washed with brine (3×150 ml), dried (MgSO$_4$) filtered and evaporated to give B as a cream powder 40.3 g (95%).

$^1$H NMR (300 MHz, CDCl$_3$) 1.66 (s,6H); 7.55 (m,2H); 8.20 (m,2H).

O-(7-Azabenzotriazol-1-yl)-N,N,N',N'-Tetramethyluronium Hexafluoro-Phosphate (89.0 g, 290 mmol) was added portion wise to a stirred, cooled (0° C.) solution of B (40.3 g, 192 mmol) in DMF (300 ml) and Diethylamine (300 ml). The resulting mixture was left to warm to RT and stir 70 hours. DMF was removed in vacuo and the residues re-dissolved in EtOAc (500 ml), washed with water (3×200 ml), brine (2×200 ml), dried MgSO$_4$, filtered and evaporated.

The crudes were purified by flash chromatography on SiO$_2$ (600 g, Merck 9385) eluting with 35% EtOAc/1-Hexane. Appropriate fractions were combined and evaporated to give C as yellow crystalline solid 44.2 g (87%).

$^1$H NMR (300 MHz, CDCl$_3$) 0.60-0.90 (m, 3H); 0.90-1.25 (m, 3H); 1.58 (s,6H); 2.65-2.95 (m, 2H); 3.20-3.45 (m, 2H); 7.40 (m, 2H); 8.20 (m, 2H).

LCMS (ES$^+$) m/z (M+H)$^+$ 265.48 (UV 254 nm 100%)

A solution of C (89.0 g, 338 mmol) in EtOH (2 L) was treated with 10% Pd/C (50% wet) (10.0 g) then stirred under H$_2$ (3 Bar) at RT for 3 hours. The RM was filtered through diatomaceous earth and evaporated to give D as a tan solid 65.5 g (83%).

$^1$H NMR (300 MHz, CDCl$_3$) 0.60-0.90 (m,3H); 0.90-1.25 (m,3H); 1.48 (s,6H); 2.80-3.10 (m,2H); 3.15-3.45 (m,2H); 3.45-3.75 (bs,2H); 6.60-6.70 (m,2H); 6.90-7.05 (m, 2H).

MS (ES$^+$) m/z (M+H)$^+$ 235.61

N-Bromosuccinimide (18.24 g, 102.6 mmol) was added portion wise to a stirred, cooled (0° C.) solution of D (24.0 g, 102.6 mmol) in CH$_2$Cl$_2$ (250 ml) and the mixture stirred for 2 hours. The RM was evaporated, the residues re-dissolved in EtOAc (200 ml), washed with saturated NaHCO$_3$ (aq) (3×200 ml), water (2×200 ml), brine (200 ml), dried MgSO$_4$, filtered and evaporated. The crudes were purified by flash chromatography on SiO$_2$ (500 g, Merck 9385) eluting with 5% MeOH/CH$_2$Cl$_2$. Appropriate fractions were combined and evaporated to give E as a tan solid 30.4 g (94.7%).

$^1$H NMR (300 MHz, CDCl$_3$) 0.60-0.90 (m,3H); 0.90-1.25 (m,3H); 1.48 (s,6H); 2.80-3.10 (m,2H); 3.15-3.50 (m,2H); 3.80-4.20 (bs,2H); 6.72 (m,1H); 6.95 (m,1H); 7.25 (m, 1H).

MS (ES$^+$) m/z (M+H)$^+$ 313.23, 315.26

A solution of E (15 g, 48 mmol) in conc HCl (48 ml) was cooled to −10° C. and to it was added drop wise a solution of NaNO$_2$ (3.97 g, 57.5 mmol) in water (24 ml) such that the internal temperature remained <−8° C. The resulting solution was left to stir for 1 hr at this temperature before it was added drop wise to a solution of SnCl$_2$.2H$_2$O (53.0 g, 235 mmol) in conc HCl (36.5 ml) at −12° C. such that the internal temperature remained <−10° C. The mixture was stirred for 2 hours at −10° C. then allowed to warm to 10° C. before it was quenched into water (600 ml), neutralised with solid NaHCO$_3$, filtered and extracted with EtOAc (3×400 ml). The organics were dried (MgSO$_4$), filtered and evaporated to a yellow oil. This was treated with 1 M HCl/Et$_2$O and dried to give the HCl salt of F as a free flowing white powder 14.7 g (84.4%)

$^1$H NMR (300 MHz, DMSO-D$_6$) 0.50-0.85 (m,3H); 0.85-1.10 (m,3H); 1.40 (s,6H); 2.70-3.00 (m,2H); 3.00-3.40(m, 2H); 7.00-7.10 (m,1H); 7.10-7.20(m, 1H); 7.20-7.30 (m,1H).

LCMS (ES$^+$) m/z (M+H)$^+$ 328.3, 330.3 (UV 254 nm 95%)

Preparation of Starting Materials (2)

Syntheses for starting materials G, H, I, J and K used in the above examples are described with reference to Scheme 6 below.

n-BuLi (1.6M in Hexanes) (100 ml, 160 mmol) was added drop wise to a stirred, cooled (−78° C.) solution of 5-Bromoxylene (21.73 ml, 160 mmol) in THF (235 ml) and Et$_2$O (235 ml) such that the internal temperature remained <−65° C. The resulting yellow suspension was allowed to stir for 1.25 hours before it was added via a cannula to a stirred, cooled (−78° C.) solution of -Butyrolactone (14.7 ml, 192 mmol) in THF (180 ml) such that the internal temperature remained <−70° C. The mixture was then stirred at this temperature for a further 5 hours, quenched with saturated NH$_4$Cl (200 ml) and extracted with Et$_2$O (3×100 ml). The combined organics were washed with brine (2×100 ml), dried (MgSO$_4$), filtered and concentrated to a yellow oil. This was then purified by chromatography on SiO$_2$ (Merck 9385) eluting with 45% EtOAc/1-Hexane to give G as a pale yellow oil 15.74 g (60%).

$^1$H NMR (300 MHz, DMSO-D$_6$) 1.70 (q,2H); 2.30 (s,6H); 2.98 (t,2H); 3.42 (q,2H); 4.43 (t,1H); 7.22 (s,1H); 7.52(s, 2H).

Diethyl Azodicarboxylate (22.5 ml, 143 mmol) was added drop wise to a stirred, cooled (−5° C.) solution of G (24.0 g, 124 mmol), Phthalimide (20.0 g, 136 mmol) and Triphenylphosphine (36.0 g, 136 mmol) in THF (450 ml) such that the internal temperature remained <0° C. The RM was stirred for 1 hr at this temperature, diluted with EtOAc (600 ml) and washed with water (250 ml) and brine (250 ml). The organics were then dried (MgSO$_4$), filtered and concentrated to a yellow semi-solid. The crudes were purified by chromatography on SiO$_2$ (Merck 9385) eluting with 25% EtOAc/1-Hexane to give H as a white powder 13.3 g (34%).

$^1$H NMR (300 MHz, DMSO-D$_6$) 1.80-2.00 (m,2H); 2.28 (s,6H); 3.03 (t,2H); 3.62 (t,2H); 7.22 (s,1H); 7.47 (s,2H); 7.70 7.90 (m, 4H).

BF$_3$.Et$_2$O (30 ml) was added to a stirred solution of F (27.0 g, 74 mmol) and H (24.4 g, 77 mmol) in AcOH (450 ml) and the resulting mixture heated at 90° C. for 48 hours. The RM was evaporated to dryness and the residues treated with saturated NaHCO$_3$ (100 ml). The resulting solids were collected by filtration, triturated with MeOH/CHCl$_3$ and re-filtered. The filtrates were concentrated to give I as an off-white powder 36 g (79%).

$^1$H NMR (300 MHz, CDCl$_3$) 0.60-0.75(m,3H); 1.00-1.15 (m,3H); 1.54 (s,6H); 2.25 (s,6H); 2.80-2.95 (m,2H); 3.24-3.40 (m,2H); 3.15-3.23 (m, 2H); 3.80-3.90 (m,2H); 6.80 (s,1H); 7.06 (s,2H); 7.12 (s,1H); 7.45 (s,1H); 7.55-7.70 (m,4H); 8.02 (s,1H).

LCMS (ES$^+$) m/z (M+H)$^+$ 613.9, 615.9 (UV 254 nm 100%)

A solution of I (42.0 g, 68 mmol) in MeOH (1000 ml) and Et$_3$N (10 ml) was treated with 10% Pd/C (10.0 g) and stirred under H$_2$ (2 Bar) for 48 hours. The catalyst was removed by filtration through diatomaceous earth and the filtrates evaporated. The residues were re-dissolved in EtOAc, washed with water, dried (MgSO$_4$), filtered and concentrated in vacuo to give J as a yellow foam 32.2 g (88%).

$^1$H NMR (300 MHz, CDCl$_3$) 0.60-0.80 (m,3H); 1.05-1.25 (m,3H); 1.60 (s,6H); 2.30 (s,6H); 2.85-3.05 (m,2H); 3.20-3.50 (m,4H); 3.90-4.00 (m, 2H); 6.85 (s,1H); 6.95-7.05 (m,1H); 7.12 (s,2H); 7.20-7.35 (m,1H+CHCl$_3$); 7.55-7.7 (m,3H); 7.70-7.80 (m,2H); 8.00 (s,1H).

LCMS (ES⁺) m/z (M+H)⁺ 536.59 (UV 254 nm 100%)

LCMS (ES⁻) m/z (M–H)⁻ 534.58 (UV 254 nm 100%)

Hydrazine Hydrate (40 ml, 192 mmol) was added to a stirred solution of J (28 g, 52.3 mmol) in a mixture of MeOH (200 ml) and CH₂Cl₂ (200 ml) and stirred for 48 hours at RT. A further portion of Hydrazine Hydrate (40 ml) was added and stirring continued for another 24 hours. The RM was filtered, washed with saturated NaHCO₃ (4×150 ml), brine (2×100 ml), dried (MgSO₄), filtered and evaporated. The crudes were purified by flash chromatography on SiO₂ (Merck 9385) eluting with EtOAc followed by 10% MeOH/ CH₂Cl₂ to give K as a pale yellow foam 17.1 g (80.6%).

¹H NMR (300 MHz, CDCl₃) 0.60-0.80 (m,3H); 1.05-1.25 (m,3H); 1.60 (s,6H); 1.76 (s,2H+H₂O); 2.38 (s,6H); 2.80-3.12 (m,6H); 3.25-3.45 (m, 2H); 7.00 (s,1H); 7.02-7.07(m, 1H); 7.17 (s,2H); 7.25-7.35 (m,1H); 7.42 (s,1H); 8.12 (s,1H).

LCMS (ES⁺) m/z (M+H)⁺ 406.56 (UV 254 nm 100%)

LCMS (ES⁻) m/z (M–H)⁻ 404.57 (UV 254 nm 100%)

Diphenyl cyanocarbonimidate (1.5 g, 6.3 mmol) was added to a stirred solution of K (1.5 g, 3.7 mmol) in IPA and the mixture stirred 18 hours at RT. The RM was concentrated in vacuo and the residues re-dissolved in EtOAc (150 ml). The organics were washed with saturated NaHCO₃ (3×70 ml), brine (2×75 ml), dried (MgSO₄), filtered and evaporated. The crudes were purified by flash chromatography on SiO₂ (Merck 9385) eluting with a gradient 0-5% MeOH/ CH₂Cl₂ to give L as an off-white foam 1.9 g (95.4%).

¹H NMR (300 MHz, CDCl₃) 0.60-0.80 (m,3H); 1.00-1.20 (m,3H); 1.55(s,6H); 2.35 (s,6H); 2.75-3.20 (m,2H); 3.10-3.45 (m, 4H); 3.60-3.75 (m,2H); 6.30-6.45 (m,1H); 6.67-6.80 (m,2H); 7.00-7.50 (m,9H); 8.18 (s,1H).

MS (ES⁺) m/z (M+H)⁺ 550.36

MS (ES⁻) m/z (M–H)⁻ 548.30, 454.38

1,1 Bis(methylthio)-2-nitroethylene (515 mg, 3.1 mmol) was added to a stirred solution of K (1.1 g, 2.72 mmol) in CH₃CN (70 ml) and heated at reflux for 18 hours. The RM was concentrated in-vacuo and the crudes purified by chromatography on SiO₂ (Merck 9385), eluting with 5% MeOH/ CH₂Cl₂ to give M as a yellow foam 1.4 g (98%).

¹H NMR (300 MHz, CDCl₃) 0.60-0.80 (m,3H); 1.05-1.25 (m,3H); 1.60 (s,6H); 2.38(s,6H); 2.80-3.05 (m,2H); 3.25-3.50 (m, 4H); 3.68 (q,2H); 6.42 (s,1H); 7.05 (s,1H); 7.06-7.15 (m,3H); 7.32 (d,1H); 7.45 (s,1H); 8.11 (s,1H).

MS (ES⁺) m/z (M+H)⁺ 523.44

MS (ES⁻) m/z (M–H)⁻ 521.49

Scheme 1

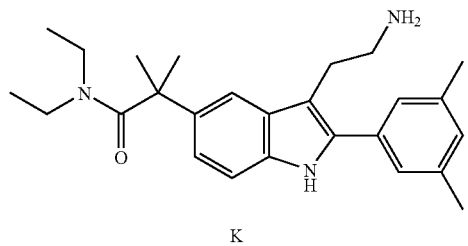

K

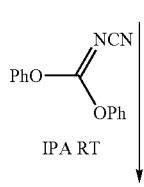

IPA RT

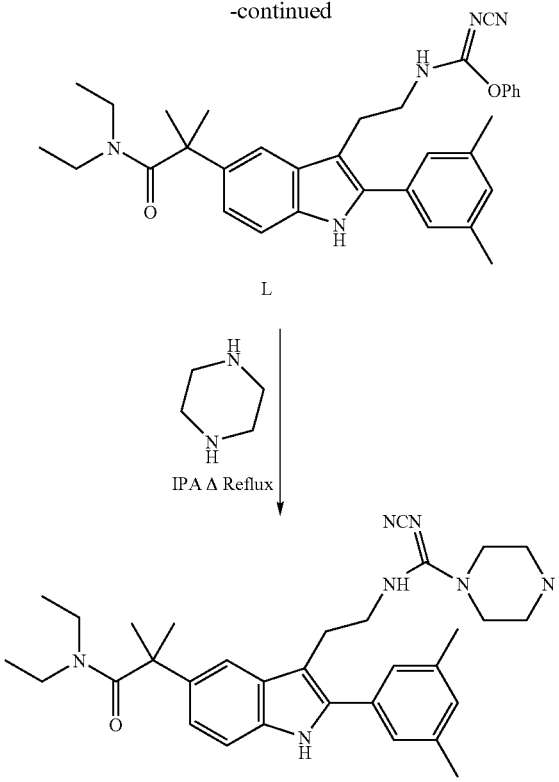

L

IPA Δ Reflux

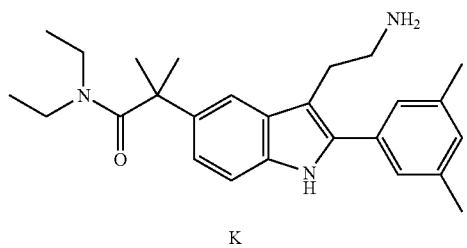

EXAMPLE 1.01

Scheme 2

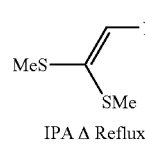

K

IPA Δ Reflux

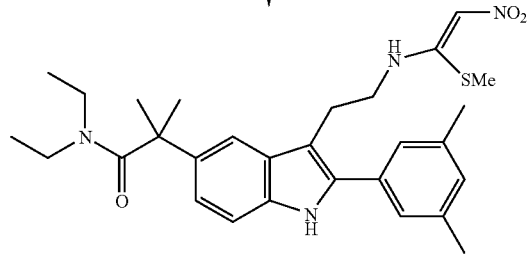

M

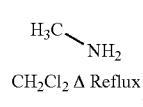

CH₂Cl₂ Δ Reflux

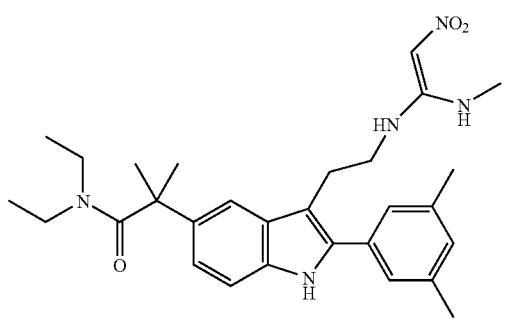

EXAMPLE 2.01

Scheme 3

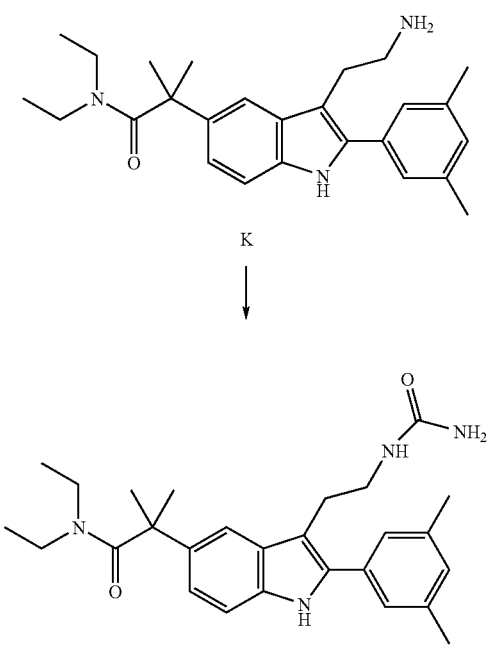

K

↓

EXAMPLE 3

Scheme 4

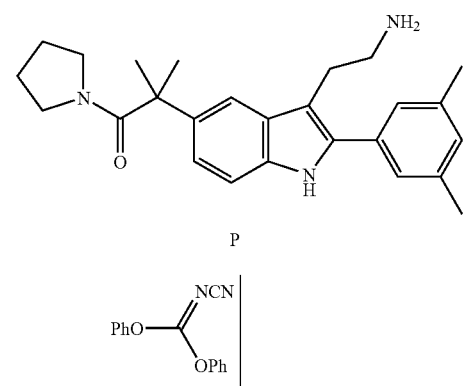

P

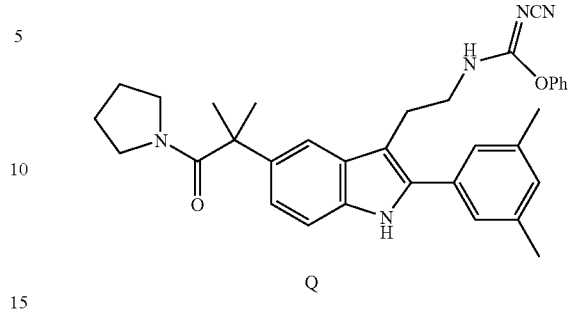

Q

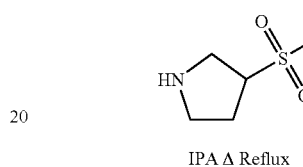

IPA Δ Reflux

↓

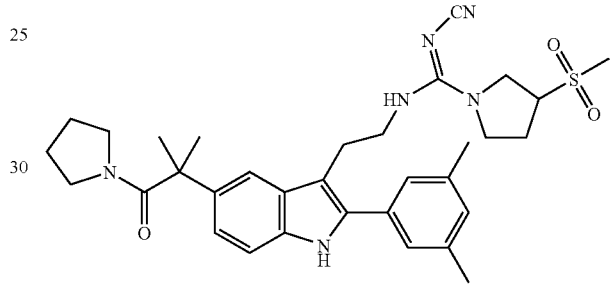

EXAMPLE 4

Therapeutic Uses

Compounds of formula I are provided as medicaments for antagonising gonadotropin releasing hormone (GnRH) activity in a patient, eg, in men and/or women. To this end, a compound of formula I can be provided as part of a pharmaceutical formulation which also includes a pharmaceutically acceptable diluent or carrier (eg, water). The formulation may be in the form of tablets, capsules, granules, powders, syrups, emulsions (eg, lipid emulsions), suppositories, ointments, creams, drops, suspensions (eg, aqueous or oily suspensions) or solutions (eg, aqueous or oily solutions). If desired, the formulation may include one or more additional substances independently selected from stabilising agents, wetting agents, emulsifying agents, buffers, lactose, sialic acid, magnesium stearate, terra alba, sucrose, corn starch, talc, gelatin, agar, pectin, peanut oil, olive oil, cacao butter and ethylene glycol.

The compound is preferably orally administered to a patient, but other routes of administration are possible, such as parenteral or rectal administration. For intravenous, subcutaneous or intramuscular administration, the patient may receive a daily dose of 0.1 mgkg$^{-1}$ to 30 mgkg$^{-1}$ (preferably, 5 mgkg$^{-1}$ to 20 mgkg$^{-1}$) of the compound, the compound being administered 1 to 4 times per day. The intravenous, subcutaneous and intramuscular dose may be given by means of a bolus injection. Alternatively, the intravenous dose may be given by continuous infusion over a period of time. Alternatively, the patient may receive a daily oral dose which is approximately equivalent to the daily parenteral dose, the composition being administered 1 to 4 times per day. A suitable pharmaceutical formulation is one suitable for oral administration in unit dosage form, for example as a tablet or capsule, which contains between 10 mg and 1 g (preferably, 100 mg and 1 g) of the compound of the invention.

The following illustrate representative pharmaceutical dosage forms containing a compound of the invention, or a pharmaceutically acceptable salt or solvate thereof (hereafter referred to as "compound X"), for use in humans.

(a)

| Tablet I | mg/tablet |
| --- | --- |
| Compound X. | 100 |
| Lactose Ph.Eur. | 179 |
| Croscarmellose sodium | 12.0 |
| Polyvinylpyrrolidone | 6 |
| Magnesium stearate | 3.0 |

(b)

| Tablet II | mg/tablet |
| --- | --- |
| Compound X | 50 |
| Lactose Ph.Eur. | 229 |
| Croscarmellose sodium | 12.0 |
| Polyvinylpyrrolidone | 6 |
| Magnesium stearate | 3.0 |

(c)

| Tablet III | mg/tablet |
| --- | --- |
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

(d)

| Capsule | mg/capsule |
| --- | --- |
| Compound X | 10 |
| Lactose Ph.Eur. | 389 |
| Croscarmellose sodium | 100 |
| Magnesium stearate | 1. |

(e)

| Injection I | (50 mg/ml) |
| --- | --- |
| Compound X | 5.0% w/v |
| Isotonic aqueous solution | to 100% |

Buffers, pharmaceutically acceptable co-solvents (eg, polyethylene glycol, propylene glycol, glycerol or EtOH) or complexing agents such as hydroxy-propyl β cyclodextrin may be used to aid formulation.

One aspect of the invention relates to the use of compounds according to the invention for reducing the secretion of LH and/or FSH by the pituitary gland of a patient. In this respect, the reduction may be by way of a reduction in biosynthesis of the LH and FSH and/or a reduction in the release of LH and FSH by the pituitary gland. Thus, compounds according to the invention can be used for therapeutically treating and/or preventing a sex hormone related condition in the patient. By "preventing" we mean reducing the patient's risk of contracting the condition. By "treating" we mean eradicating the condition or reducing its severity in the patient. Examples of sex hormone related conditions are: a sex hormone dependent cancer, benign prostatic hypertrophy, myoma of the uterus, endometriosis, polycystic ovarian disease, uterine fibroids, prostatauxe, myoma uteri, hirsutism and precocious puberty. Examples of sex hormone dependent cancers are: prostatic cancer, uterine cancer, breast cancer and pituitary gonadotrophe adenoma.

The compounds of the invention may be used in combination with other drugs and therapies used to treat/prevent sex-hormone related conditions.

If formulated as a fixed dose such combination products employ the compounds of this invention within the dosage range described herein and the other pharmaceutically-active agent within its approved dosage range. Sequential use is contemplated when a combination formulation is inappropriate.

In the field of medical oncology examples of such combinations include combinations with the following categories of therapeutic agent:

i) anti-angiogenic agents (for example linomide, inhibitors of integrin αvβ3 function, angiostatin, endostatin, razoxin, thalidomide) and including vascular endothelial growth factor (VEGF) receptor tyrosine kinase inhibitors (RTKIs) (for example those described in international patent applications publication nos. WO-97/22596, WO-97/30035, WO-97/32856 and WO-98/13354, the entire disclosure of which documents is incorporated herein by reference);

ii) cytostatic agents such as anti-oestrogens (for example tamoxifen, toremifene, raloxifene, droloxifene, iodoxyfene), progestogens (for example megestrol acetate), aromatase inhibitors (for example anastrozole, letrozole, vorazole, exemestane), anti-progestogens, anti-androgens (for example flutamide, nilutamide, bicalutamide, cyproterone acetate), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

iii) biological response modifiers (for example interferon);

iv) antibodies (for example edrecolomab); and v) anti-proliferative/anti-neoplastic drugs and combinations thereof, as used in medical oncology, such as anti-metabolites (for example anti-folates like methotrexate, fluoropyrimidines like 5-fluorouracil, purine and adenosine analogues, cytosine arabinoside); anti-tumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); anti-mitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

The compounds of the invention may also be used in combination with surgery or radiotherapy.

Assays

The ability of compounds according to the invention to act as antagonists of GnRH can be determined using the following in vitro assays.

Binding Assay Using Rat Pituitary GnRH Receptor

The assay is performed as follows:—
1. Incubate crude plasma membranes prepared from rat pituitary tissues in a Tris.HCl buffer (pH. 7.5, 50 mM) containing bovine serum albumin (0.1%), [I-125]D-t-Bu-Ser6-Pro9-ethyl amide-GnRH, and the test compound. Incubation is at 4° C. for 90 minutes to 2 hours.
2. Rapidly filter and repeatedly wash through a glass fibre filter.
3. Determine the radioactivity of membrane bound radio-ligands using a gamma counter.

From this data, the $IC_{50}$ of the test compound can be determined as the concentration of the compound required to inhibit radio-ligand binding to GnRH receptors by 50%. Compounds according to the present invention have activity at a concentration from 1 nM to 5 µM.

Binding Assay Using Human GnRH Receptor

Crude membranes prepared from CHO cells expressing human GnRH receptors are sources for the GnRH receptor. The binding activity of compounds according to the invention can be determined as an $IC_{50}$ which is the compound concentration required to inhibit the specific binding of [$^{125}$I]buserelin to GnRH receptors by 50%. [$^{125}$I]Buserelin (a peptide GnRH analogue) is used here as a radiolabelled ligand of the receptor.

Assay to Determine Inhibition of LH Release

The LH release assay can be used to demonstrate antagonist activity of compounds, as demonstrated by a reduction in GnRH-induced LH release.

Preparation of Pituitary Glands

Pituitary glands obtained from rats are prepared as follows. Suitable rats are Wistar male rats (150-200 g) which have been maintained at a constant temperature (eg, 25° C.) on a 12 hour light/12 hour dark cycle. The rats are sacrificed by decapitation before the pituitary glands are aseptically removed to tube containing Hank's Balanced Salt Solution (HBSS). The glands are further processed by:—
1. Centrifugation at 250×g for 5 minutes;
2. Aspiration of the HBSS solution;
3. Transfer of the glands to a petri dish before mincing with a scalpel;
4. Transfer of the minced tissue to a centrifuge tube by suspending the tissue three successive times in 10 ml aliquots of HBSS containing 0.2% collagenase and 0.2% hyaluronidase;
5. Cell dispersion by gentle stirring of the tissue suspension while the tube is kept in a water bath at 37° C.;
6. Aspiration 20 to 30 times using a pipette, undigested pituitary fragments being allowed to settle for 3 to 5 minutes;
7. Aspiration of the suspended cells followed by centrifugation at 1200×g for 5 minutes;
8. Re-suspension of the cells in culture medium of DMEM containing 0.37% $NaHCO_3$, 10% horse serum, 2.5% foetal bovine serum, 1% non essential amino acids, 1% glutamine and 0.1% gentamycin;
9. Treatment of the undigested pituitary fragments 3 times with 30 ml aliquots of the collagenase and hyaluronidase;
10. Pooling of the cell suspensions and dilution to a concentration of $3 \times 10^5$ cells/ml;
11. Placing of 1.0 ml of this suspension in each of a 24 well tray, with the cells being maintained in a humidified 5% $CO_2$/95% air atmosphere at 37° C. for 3 to 4 days Testing of Compounds The test compound is dissolved in DMSO to a final concentration of 0.5% in the incubation medium.

1.5 hours prior to the assay, the cells are washed three times with DMEM containing 0.37% $NaHCO_3$, 10% horse serum, 2.5% foetal bovine serum, 1% non essential amino acids (100×), 1% glutamine (100×), 1% penicillin/streptomycin (10,000 units of each per ml) and 25 mM HEPES at pH 7.4. Immediately prior to the assay, the cells are again washed twice in this medium.

Following this, 1 ml of fresh medium containing the test compound and 2 nM GnRH is added to two wells. For other test compounds (where it is desired to test more than one compound), these are added to other respective duplicate wells. Incubation is then carried out at 37° C. for three hours.

Following incubation, each well is analysed by removing the medium from the well and centrifuging the medium at 2000×g for 15 minutes to remove any cellular material. The supernatant is removed and assayed for LH content using a double antibody radio-immuno assay. Comparison with a suitable control (no test compound) is used to determine whether the test compound reduces LH release. Compounds according to the present invention have activity at a concentration from 1 nM to 5 µM.

The invention claimed is:

1. A compound of formula I or a salt, pro-drug or solvate thereof

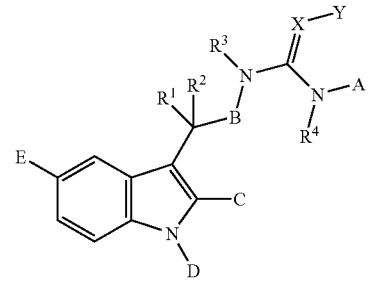

formula I wherein
for A, either:—
  (i) A represents hydrogen or optionally substituted $C_1$ to $C_8$ alkyl; or
  (ii) the structure N—A(—$R^4$) represents an optionally substituted 3- to 8-membered heterocyclic ring optionally containing from 1 to 3 further heteroatoms independently selected from O, N and S;
B represents a direct bond or optionally substituted $C_1$ to $C_5$ alkylene;
C represents a mono- or bi-cyclic aromatic ring structure optionally having at least one substituent selected from CN, $NR^5R^6$, an optionally substituted $C_1$ to $C_8$ alkyl, optionally substituted $C_1$ to $C_8$ alkoxy or halo;
D represents hydrogen; optionally substituted $C_1$ to $C_8$ alkyl; or $(CH_2)_b$—$R^a$, wherein $R^a$ is $C_3$ to $C_8$ cycloalkyl and b represents zero or an integer from 1 to 6;
E is selected from an optionally substituted 3- to 8-membered heterocyclic ring containing from 1 to 4 heteroatoms independently selected from O, N and S; or a group of formula II; III; IV; V; VI, VII or VIII

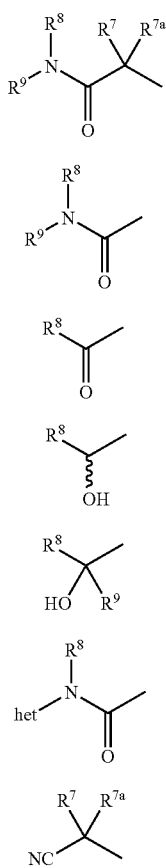

II

III

IV

V

VI

VII

VIII wherein het represents an optionally substituted 3- to 8-membered heterocyclic ring containing from 1 to 4 heteroatoms independently selected from O, N and S;
for X and Y, either:—
- (iii) X represents N and Y represents CN; hydrogen or —CONR$^b$R$^c$ where R$^b$ and R$^c$ are independently selected from hydrogen and C$_1$ to C$_8$ alkyl;
- (iiia) X represents CH and Y represents NO$_2$; or
- (iv) X—Y represents O;

For R$^1$ and R$^2$, either:—
- (v) R$^1$ and R$^2$ are independently selected from hydrogen and optionally substituted C$_1$ to C$_8$ alkyl; or
- (vi) R$^1$ and R$^2$ together represent carbonyl; or
- (vii)

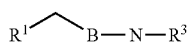

represents an optionally substituted 3- to 8-membered heterocyclic ring containing from 1 to 3 further heteroatoms independently selected from O, N and S, and R$^2$ meets the definition in option (v);
- R$^3$ meets the definition in option (vii) or represents hydrogen or optionally substituted C$_1$ to C$_8$ alkyl;
- R$^4$ meets the definition in option (ii), or when A meets the definition in option (i) R$^4$ represents hydrogen or optionally substituted C$_1$ to C$_8$ alkyl;
- R$^5$ and R$^6$ are independently selected from hydrogen; optionally substituted C$_1$ to C$_8$ alkyl and optionally substituted aryl;

for R$^7$ and R$^{7a}$, either:—
- (viii) R$^7$ and R$^{7a}$ are independently selected from hydrogen or optionally substituted C$_1$ to C$_8$ alkyl; or
- (ix)

represents an optionally substituted 3 to 7-membered cycloalkyl ring;
for R$^8$ and R$^9$, either:—
- (x) R$^8$ is selected from hydrogen; optionally substituted C$_1$ to C$_8$ alkyl; optionally substituted aryl; —R$^d$—Ar, where R$^d$ represents C$_1$ to C$_8$ alkylene and Ar represents optionally substituted aryl;
  and an optionally substituted 3- to 8-membered heterocyclic ring optionally containing from 1 to 3 further heteroatoms independently selected from O, N and S; and
  R$^9$ is selected from hydrogen; optionally substituted C$_1$ to C$_8$ alkyl and optionally substituted aryl;
- (xi) wherein E represents a group of formula II or III, then the group NR$^8$(—R$^9$) represents an optionally substituted 3- to 8-membered heterocyclic ring optionally containing from 1 to 3 further heteroatoms independently selected from O, N and S; or
- (xii) wherein E represents structure VI,

represents an optionally substituted 3- to 8-membered heterocyclic ring optionally containing from 1 to 4 heteroatoms independently selected from O, N and S;
with the proviso that:
when A is C$_1$ to C$_8$ alkyl or the structure N—A(—R$^4$) represents an optionally-substituted 3- to 8-membered heterocyclic ring containing from 1 to 3 heteroatoms independently selected from O, N and S; X represents N and Y represents CN or hydrogen, X represents CH and Y represents NO$_2$ or X—Y represents O; then the optional substituents on A are not selected from optionally substituted phenyl or an optionally-substituted 3- to 8-membered heterocyclic ring.

2. The compound of claim 1, wherein —N—A(—R$^4$) meets the definition in option (ii) and is selected from an optionally-substituted group of formula IX, X or Xi,

IX

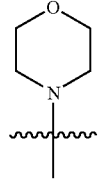

X

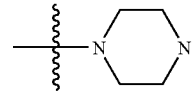

-continued

XI

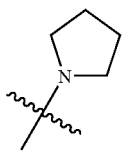

3. The compound of claim 2, wherein —N—A(—R⁴) is selected from XII or XIII

XII

XIII

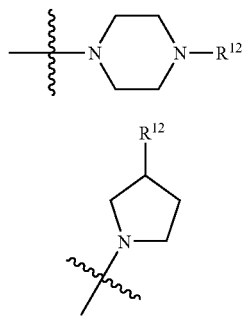

wherein
R¹² represents $C_1$ to $C_8$ alkyl; —$(CH_2)_c NR^e R^f$, where c is zero or an integer from 1 to 4, and $R^e$ and $R^f$ independently represent hydrogen or $C_1$ to $C_8$ alkyl; hydroxy; halo; CN; $C_1$ to $C_8$ alkoxy; or $CF_3$.

4. The compound of claim 1, wherein A and R⁴ each represent hydrogen.

5. The compound of claim 1, wherein, E represents
(a) structure II of the sub-formula

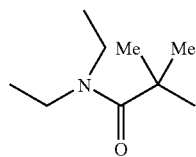

wherein Me represents methyl;
(b) structure II, wherein

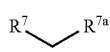

represents cyclopropyl or cyclobutyl; or
(c) structure VIII wherein R⁷ and $R^{7a}$ each represent methyl.

6. The compound of claim 1, wherein C represents

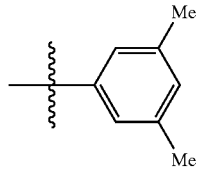

wherein Me represents methyl.

7. The compound of claim 1, wherein R¹ and R² each represent hydrogen and B represents $C_1$ alkylene.

8. The compound of claim 1, wherein the compound is selected from a compound of formula XXI to XXXI

XXI

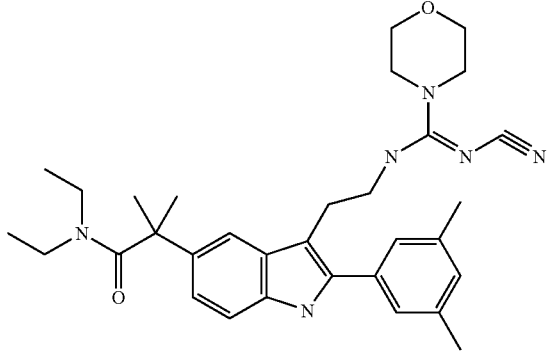

XXII

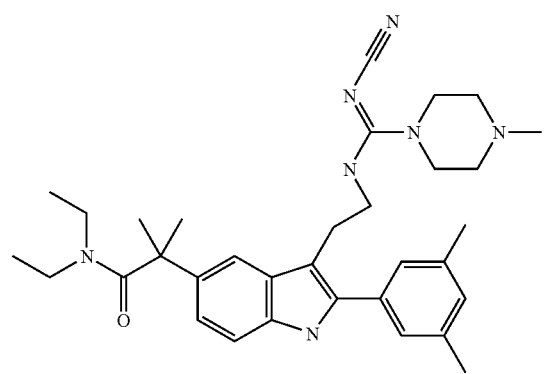

XXIII

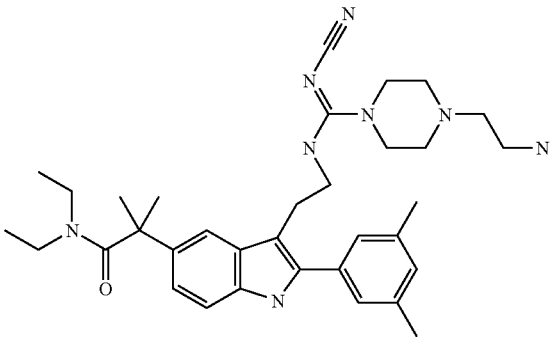

XXIV

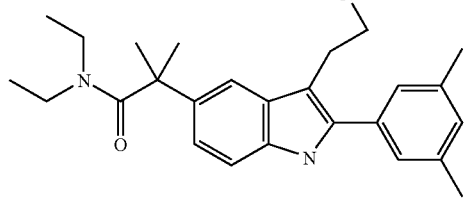

XXV

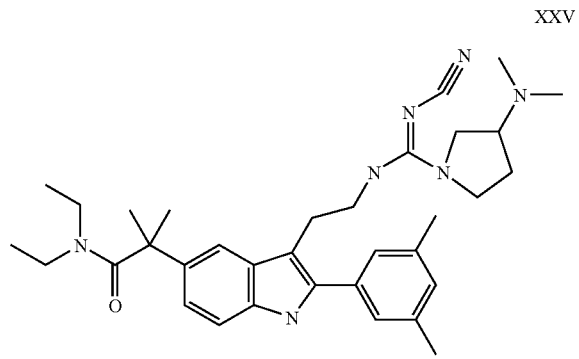

XXVI

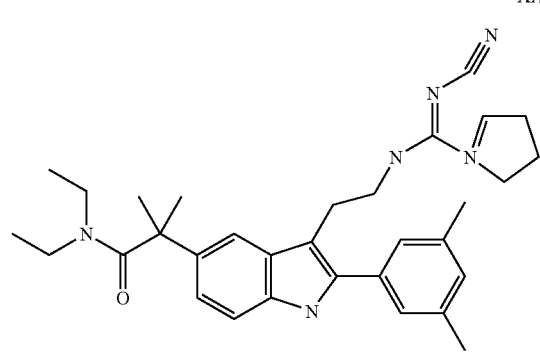

XXVII

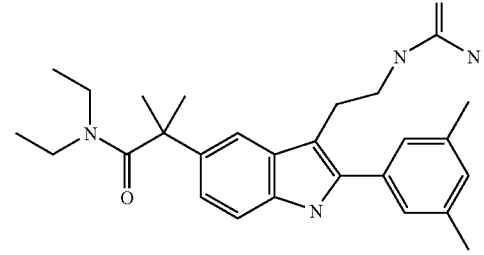

XXVIII

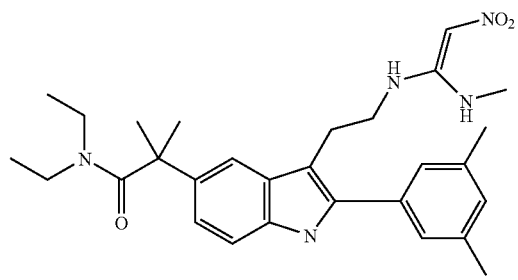

XXIX

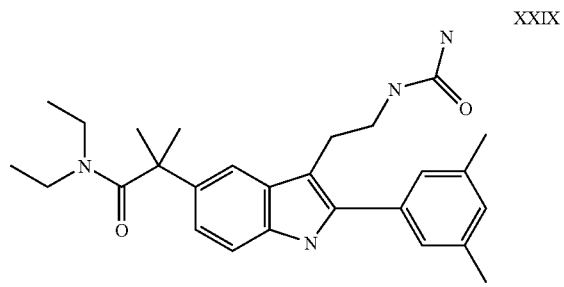

XXX

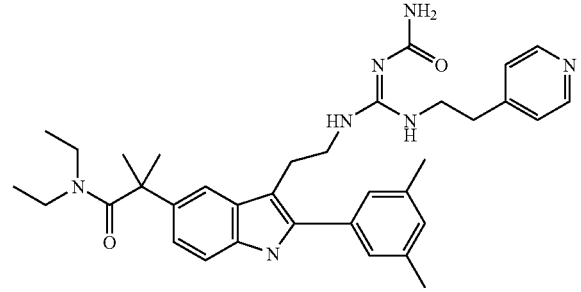

XXXI

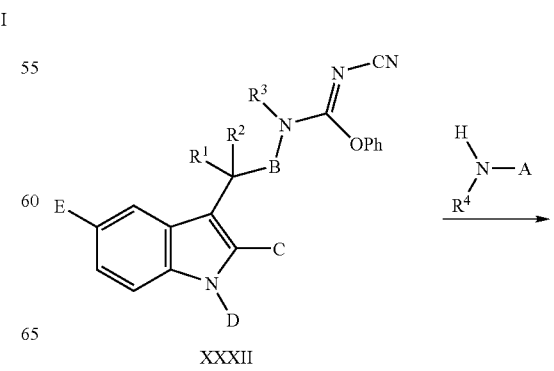

or salt, pro-drug or solvate thereof.

9. A pharmaceutical formulation comprising a compound, or salt, pro-drug or solvate thereof, according to claim 1 and a pharmaceutically acceptable diluent or carrier.

10. A process of producing a compound, or salt, pro-drug or solvate thereof, according to claim 1, wherein the process comprises a reaction selected from any one of (a) to (e):—

(a) Reaction of a compound of formula XXXII as follows

-continued

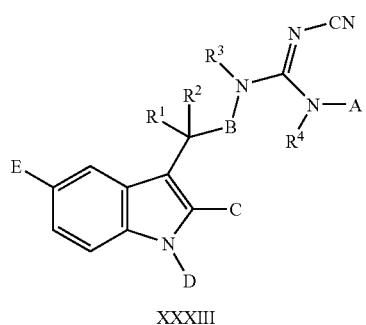

XXXIII (b) Cleavage of the CN group of a compound of formula XXXIII in the presence of acid to produce a compound of formula XXXIV

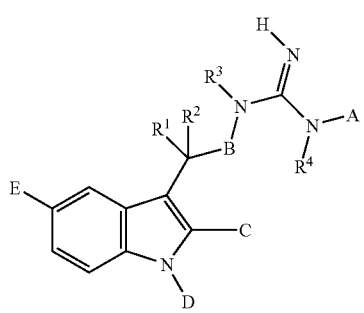

XXXIV (c) Reaction of a compound of formula XXXV as follows

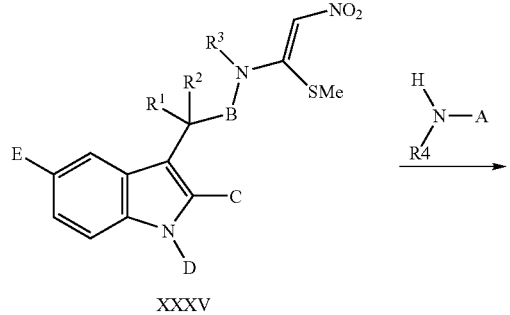

XXXV

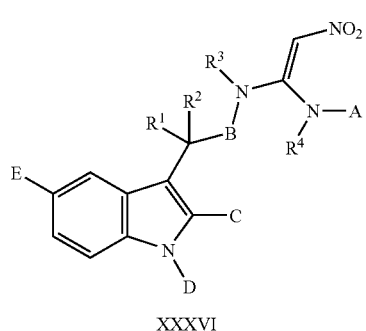

XXXVI (d) Reaction of a compound of formula XXXVII as follows

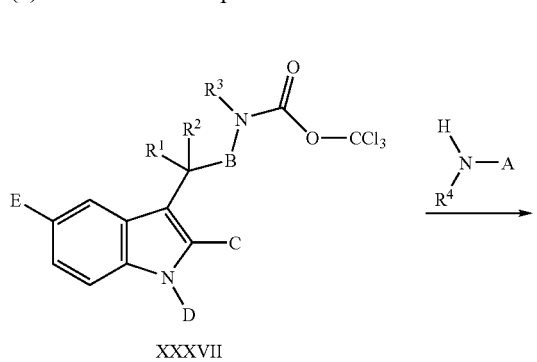

XXXVII

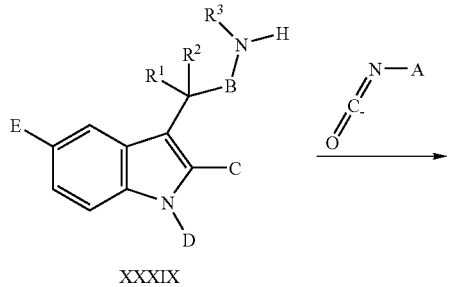

XXXVIII (e) Reaction of a compound of formula XXXIX as follows

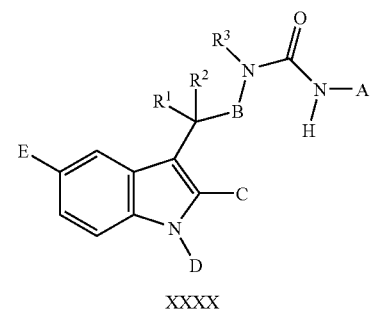

XXXIX

XXXX and thereafter, optionally:
i) converting a compound of the formula I into another compound of the formula I;
ii) removing any protecting groups;
iii) forming a salt, pro-drug or solvate.

* * * * *